(12) United States Patent
Kobori et al.

(10) Patent No.: US 7,183,299 B2
(45) Date of Patent: Feb. 27, 2007

(54) TETRAZOYL OXIME DERIVATIVE AND AGRICULTURAL CHEMICAL CONTAINING THE SAME AS ACTIVE INGREDIENT

(75) Inventors: Takeo Kobori, Inba-gun (JP); Hitoshi Kondo, Chiba (JP); Hiroyuki Tsuboi, Yachiyo (JP); Kumiko Akiba, Chiba (JP); Akihiro Koiso, Sakura (JP); Tsuneyuki Otaguro, Sakura (JP); Hidetoshi Nakayama, Chiba (JP); Hiroyuki Hamano, Sakura (JP); Akira Ohno, Chiba (JP); Toru Asada, Inba-gun (JP)

(73) Assignee: Nippon Soda Co., Ltd., Tokyo (JP)

( * ) Notice: Subject to any disclaimer, the term of this patent is extended or adjusted under 35 U.S.C. 154(b) by 173 days.

(21) Appl. No.: 10/486,205

(22) PCT Filed: Aug. 16, 2002

(86) PCT No.: PCT/JP02/08319

§ 371 (c)(1),
(2), (4) Date: Feb. 13, 2004

(87) PCT Pub. No.: WO03/016303

PCT Pub. Date: Feb. 27, 2003

(65) Prior Publication Data

US 2005/0070439 A1 Mar. 31, 2005

(30) Foreign Application Priority Data

Aug. 20, 2001 (JP) ............................... 2001-249006

(51) Int. Cl.
*C07D 401/02* (2006.01)
*C07D 401/12* (2006.01)
*C07D 417/12* (2006.01)
*A01N 43/82* (2006.01)

(52) U.S. Cl. ...................... 514/361; 514/362; 514/364; 514/340; 514/342; 546/177; 546/277; 548/127; 548/134

(58) Field of Classification Search ................ 548/240, 548/243, 247, 127, 134, 125; 514/378, 380, 514/361, 362, 364, 340, 342; 546/177, 277
See application file for complete search history.

(56) References Cited

U.S. PATENT DOCUMENTS 6,048,885 A * 4/2000 Takase et al. ............... 514/378
6,340,697 B1 * 1/2002 Kobori et al. .............. 514/364

FOREIGN PATENT DOCUMENTS

| EP | 532127 A1 | 3/1993 |
|---|---|---|
| EP | 1038874 A1 | 9/2000 |
| EP | 1184382 A1 | 3/2002 |
| HU | 183240 B | 4/1984 |
| HU | 201223 B | 10/1990 |
| HU | 209642 | 5/1995 |
| JP | 7-252242 | 10/1995 |
| JP | 2000-351772 | 12/2000 |
| WO | WO 99/29689 A1 | 6/1999 |
| WO | WO 00/75138 A1 | 12/2000 |

OTHER PUBLICATIONS

Abstract of WO 95/26956 A1 dated Oct. 12, 1995/Cited in the International Search Report./Corresponds to USP 6048885.
R. Raap; "Reactions of 1-Substituted 5-Tetrazolyllithium Compounds; Preparation of 5-Substituted 1-Methyltetrazoles"; *Canadian Journal of Chemistry*; vol. 49; 1971; pp. 2139-2142.
J. Plenkiewicz et al.; "Synthesis and Thermolysis of Some N-Hydroximoyl-and N-Hydrazonoylazoles"; *Bull. Soc. Chim. Belg.*; vol. 96; No. 9; 1987; pp. 675-709./Cited in the International Search Report.
Hungarian Search Report and English translation received Oct. 24, 2005.

* cited by examiner

*Primary Examiner*—Sabiha N. Qazi
(74) *Attorney, Agent, or Firm*—Armstrong, Kratz, Quintos, Hanson, Brooks, LLP

(57) ABSTRACT

The present invention provides a tetrazoyloxime derivative which is less likely to cause chemical injury to useful plants and is also superior in chemical efficacy to a conventional hetero ring-substituted oxime derivative. A tetrazoyloxime derivative represented by the general formula (1):

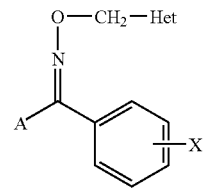

X represents a hydrogen atom, a halogen atom, an alkyl group, an alkoxy group, a cyano group, a methanesulfonyl group, a nitro group, a trifluoromethyl group, or an aryl group; A represents a 1-alkyltetrazoyl-5-yl group or a 5-alkyltetrazoyl-1-yl group; and Het represents a pyridyl group having a substituent or a thiazoyl group having a substituent, and a plant disease controlling agent containing the same as an active ingredient are disclosed.

11 Claims, No Drawings

TETRAZOYL OXIME DERIVATIVE AND AGRICULTURAL CHEMICAL CONTAINING THE SAME AS ACTIVE INGREDIENT

TECHNICAL FIELD

The present invention relates to a novel tetrazoyloxime derivative and to an agricultural chemical containing the same as an active ingredient and, more particularly, to a plant disease controlling agent.

BACKGROUND ART

Japanese Unexamined Patent Application, First Publication No. Hei 11-269176 (WO99/29689, EP-A-1038874) and Japanese Unexamined Patent Application, First Publication No. 2001-55387 (WO00/75138, EP-A-1184382) according to an invention of the present inventors disclose that hetero ring-substituted oxime derivatives act as plant disease controlling agents.

Specifically, Japanese Unexamined Patent Application, First Publication No. Hei 11-269176 (WO99/29689, EP-A-1038874) discloses oxime derivatives represented by the general formula (A):

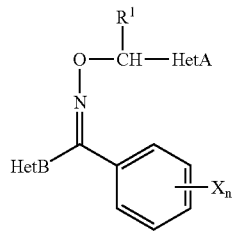

(A)

wherein $R^1$ represents a hydrogen atom or a lower alkyl group; X represents a halogen atom, a nitro group, a hydroxy group, a cyano group, a carboxyl group, an alkoxycarbonyl group, a lower alkyl group, a lower alkoxy group, a lower alkylthio group, a lower alkylsulfonyl group, an aryl group, an aryloxy group, or an amino group; n represents an integer of 0 to 3; Het A represents a six-membered nitrogen-containing aromatic ring having one or more nitrogen atoms, which may be substituted with one or more substituents selected from the group consisting of a halogen atom, a lower alkyl group, a lower alkylthio group, a lower alkylsulfonyl group, a lower alkoxy group, a trifluoromethyl group and a cyano group, or a benzo condensed ring type nitrogen-containing aromatic ring; and Het B represents a group represented by an one of the ring structures of the general formula:

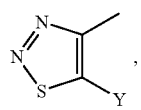

, the general formula:

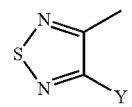

and the general formula:

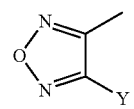

(wherein Y represents a hydrogen atom, a halogen atom, or a lower alkyl group).

Also Japanese Unexamined Patent Application, First Publication No.2001-55387 (WO00/75138, EP-A-1184382) discloses oxime derivatives represented by the general formula (B):

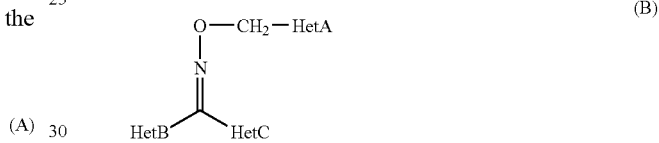

(B)

wherein Het A represents a group represented by any one of the following three formulas:

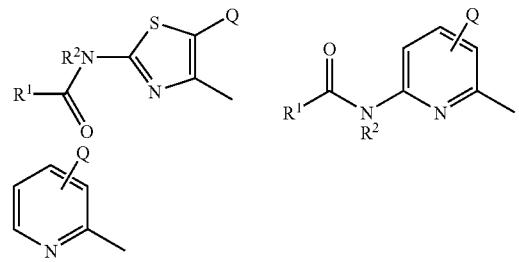

(wherein Q represents a hydrogen atom, a halogen atom, or a lower alkyl group; $R^1$ represents a hydrogen atom, a lower alkyl group, a cycloalkyl group, a lower alkenyl group, a lower alkynyl group, an aralkyl group, or an aryl group; and $R^2$ represents a hydrogen atom or a lower alkyl group); Het B represents a group represented by any one of the following nine formulas:

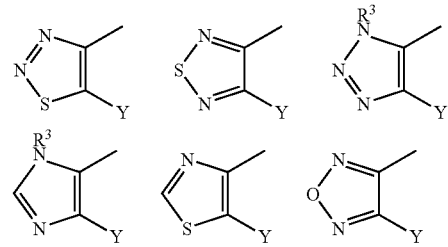

-continued

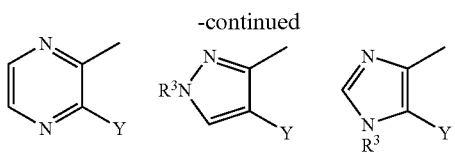

(wherein Y represents a hydrogen atom or a lower alkyl group; and $R^3$ represents a hydrogen atom or a lower alkyl group); and Het C represents a group represented by any one of the following nine formulas:

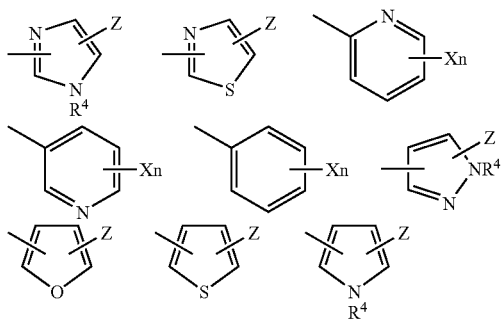

(wherein $R^4$ represents a hydrogen atom or a lower alkyl group; X represents a hydrogen atom, a halogen atom, a lower alkyl group, a lower alkoxy group, or a cyano group; Z represents a hydrogen atom, a halogen atom, or a lower alkyl group, and n represents an integer of 0 to 3).

Although the respective compounds described in Japanese Unexamined Patent Application, First Publication No. Hei 11-269176 (WO99/29689, EP-A-1038874) and Japanese Unexamined Patent Application, First Publication No. 2001-55387 (WO00/75138, EP-A-1184382) exhibit considerable control activity, it is particularly necessary to develop chemicals which exert superior control activity.

The document (Bull. Soc. Chim. Belg., Vol. 96, page 675, 1987) discloses only compounds similar to tetrazoylhydroxime derivatives represented by the general formula (7) described in claim 9 of the present invention, which are suited for use as an intermediate for synthesis of tetrazoyloxime derivatives described in claim 1 of the present invention, for example, compound of the general formula (7) $X^2$ is a hydrogen atom and $Y^2$ is a methyl group, compound wherein $X^2$ is a hydrogen atom and $Y^2$ is an isopropyl group, and compound wherein $X^2$ is a chlorine atom and $Y^2$ is a methyl group. These three compounds were synthesized during research for the purpose of elucidation of a reaction mechanism. The document does not disclose the utility of these compounds, for example, tetrazoyloxime derivatives represented by the general formula (1) described in claim 1 of the present invention can be synthesized by using the compounds and the compounds are suited for use as an intermediate for preparation of an agricultural chemical.

DISCLOSURE OF INVENTION

An object of the present invention to be achieved by the present invention is to provide tetrazoyloxime derivatives which are less likely to chemically injure useful plants and are also superior in chemical efficacy against plant diseases to conventional hetero ring-substituted oxime derivatives.

Another object to be achieved by the present invention is to provide an agricultural chemical containing the tetrazoyloxime derivatives as an active ingredient, which has sufficient plant disease controlling activity.

Still another object to be achieved by the present invention is to provide tetrazoylhydroxime derivatives suited for use as intermediates for preparation of the tetrazoyloxime derivatives.

To achieve these objects, the present inventors have synthesized various tetrazoyloxime derivatives and intensively researched their bioactivity. As a result, they have found that a tetrazoyloxime derivative represented by the following formula (1) is less likely to cause chemical injury to useful plants and also exhibits particularly superior plant disease controlling activity using small amounts thereof. Thus, the present invention has been completed.

To achieve the above object, the present invention provides a tetrazoyloxime derivative represented by the general formula (1):

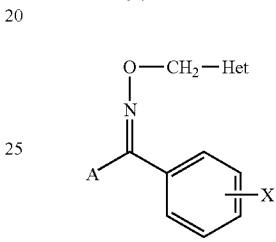

wherein X represents a hydrogen atom, a halogen atom, an alkyl group, an alkoxy group, a cyano group, a methanesulfonyl group, a nitro group, a trifluoromethyl group, or an aryl group; A represents a tetrazoyl group represented by the general formula (2):

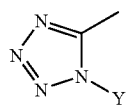

(wherein Y represents an alkyl group) or a tetrazoyl group represented by the general formula (3):

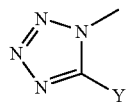

(wherein Y represents an alkyl group); and Het represents a pyridyl group represented by the general formula (4):

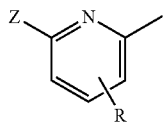

(wherein R represents a hydrogen atom or a halogen atom; Z represents a hydrogen atom, an amino group, the general formula QC(=O)NH— (Q represents a hydrogen atom, an alkyl group having 1 to 8 carbon atoms, an alkyl group having 1 to 6 carbon atoms substituted with a halogen atom, a cycloalkyl group having 3 to 6 carbon atoms, an alkoxyl group having 1 to 8 carbon atoms, a cycloalkyloxy group having 3 to 6 carbon atoms, a benzyloxy group, a 2-phenylethyloxy group, a thioalkyl group substituted with an alkyl group having 1 to 4 carbon atoms, an alkyl group having 1 to 2 carbon atoms substituted with an alkoxyl group having 1 to 4 carbon atoms, an alkyl group having 1 to 6 carbon atoms substituted with an acylamino group having 1 to 4 carbon atoms, an alkoxy group having 1 to 6 carbon atoms substituted with an acylamino group having 1 to 4 carbon atoms, an alkylamino group having 1 to 8 carbon atoms, an alkenyl group having 2 to 6 carbon atoms, an aralkyl group, or a phenyl group)), or a thiazoyl group represented by the general formula (5):

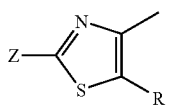

(wherein R and Z are as defined in the general formula (4).

To achieve the above object, the present invention provides a tetrazoylhydroxyimino derivative represented by the general formula (6):

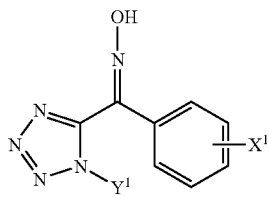

wherein $X^1$ represents a hydrogen atom, a halogen atom, an alkyl group, or an alkoxy group; and $Y^1$ represents an alkyl group, and a tetrazoylhydroxyimino derivative represented by the general formula (7):

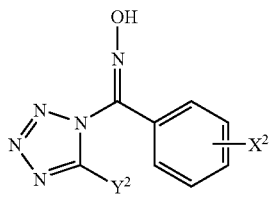

wherein $x^2$ represents an alkyl group, an alkoxy group, a cyano group, a methanesulfonyl group, a nitro group, a trifluoromethyl group, or an aryl group; and $Y^2$ represents an alkyl group, which are suited for use as an intermediate for synthesis of the tetrazoyloxime derivative represented by the general formula (1).

To achieve the above object, the present invention provides an agricultural chemical, especially a plant disease controlling agent, comprising the tetrazoyloxime derivative represented by the general formula (1) as an active ingredient.

BEST MODE FOR CARRYING OUT THE INVENTION

In the tetrazoyloxime derivative represented by the general formula (1), the substitution position of X is not specifically limited and X represents a hydrogen atom, a halogen atom, an alkyl group, an alkoxy group, a cyano group, a methanesulfonyl group, a nitro group, a trifluoromethyl group, or an aryl group.

Examples of a halogen atom for X include a chlorine atom, a bromine atom, an iodine atom, and a fluorine atom. Among these halogen atoms, a chlorine atom or a fluorine atom is particularly preferable because the resulting compound is less likely to cause chemical injury and is superior in control activity.

The alkyl group represented for X is preferably an alkyl group having 1 to 4 carbon atoms and specific examples thereof include a methyl group, an ethyl group, an n-propyl group, an isopropyl group, an n-butyl group, an isobutyl group, a sec-butyl group, and a tert-butyl group. Among these alkyl groups, a methyl group or a tert-butyl group is particularly preferable because the resulting compound is less likely to cause chemical injury and is superior in control activity.

The alkoxy group for X is preferably alkoxy group having 1 to 3 carbon atoms and specific examples thereof include a methoxy group, an ethoxy group, a propoxy group, and an isopropoxy group. Among these alkoxy groups, a methoxy group or an ethoxy group is particularly preferable because the resulting compound is less likely to cause chemical injury and is superior in control activity.

Examples of the aryl group for X include a phenyl group, a 4-methylphenyl group, and a 4-chlorophenyl group. Among these aryl groups, a phenyl group is particularly preferable because the resulting compound is less likely to cause chemical injury and is superior in control activity.

Among these, a hydrogen atom is most preferable.

In the tetrazoyl group represented by the general formula (2) or (3), Y represents an alkyl group. Among these alkyl groups, an alkyl group having 1 to 3 carbon atoms such as a methyl group, an ethyl group, an n-propyl group, or an isopropyl group is preferable. Among these alkyl groups, a methyl group or an ethyl group is particularly preferable because the resulting compound is less likely to cause chemical injury and is superior in control activity.

R in the pyridyl group represented by the general formula (4) represents a hydrogen atom, or a halogen atom such as a chlorine atom, a bromine atom, an iodine atom, or a fluorine atom. Among these, a hydrogen atom or a chlorine atom is particularly preferable because the resulting compound is less likely to cause chemical injury and is superior in control activity.

Het in the tetrazoyloxime derivative represented by the general formula (1) is either a pyridyl group represented by the general formula (4), or a thiazoyl group represented by the general formula (5), while Z in the general formulas (4) and (5) represents a hydrogen atom, an amino group, or a group represented by the general formula QC(=O)NH.

Q in the group represented by the general formula QC(=O)NH represents a hydrogen atom, a lower alkyl group, a lower alkyl group substituted with a halogen atom, a cycloalkyl group having 3 to 6 carbon atoms, a benzyloxy group, a 2-phenylethyloxy group, an alkoxy group having 1 to 8 carbon atoms, a cycloalkyloxy group having 3 to 6 carbon atoms, a lower alkyl group substituted with an alkoxy group having 1 to 6 carbon atoms, a thioalkyl group substituted with an alkyl group having 1 to 4 carbon atoms, an alkyl group having 1 to 6 carbon atoms substituted with an acylamino group having 1 to 4 carbon atoms, an alkoxy group having 1 to 6 carbon atoms substituted with an acylamino group having 1 to 4 carbon atoms, an alkylamino group having 1 to 8 carbon atoms, an alkenyl group having 2 to 6 carbon atoms, an aralkyl group, or a phenyl group.

The lower alkyl group for Q is preferably an alkyl group having 1 to 8 carbon atoms and specific examples thereof include a methyl group, an ethyl group, an n-propyl group, an isopropyl group, a 1,1-dimethylpropyl group, an n-butyl group, an isobutyl group, a sec-butyl group, a tert-butyl group, an isoamyl group, a 1-methylbutyl group, a 2-methylbutyl group, an neopentyl group, a 1-ethylpropyl group, an n-pentyl group, a hexyl group, a heptyl group, and an octyl group.

The lower alkyl group substituted with the halogen atom for Q is preferably an alkyl group having 1 to 6 carbon atoms substituted with a halogen atom and specific examples thereof include a chloromethyl group, a difluoromethyl group, a trifluoromethyl group, a difluorochloromethyl group, a pentafluoroethyl group, a 3,3,3-trifluoro-n-propyl group, and a 1-chlorohexyl group.

Specific examples of the cycloalkyl group having 3 to 6 carbon atoms for Q include a cyclopropyl group, a cyclobutyl group, a cyclopentyl group, and a cyclohexyl group.

Specific examples of the alkoxy group having 1 to 8 carbon atoms for Q include a methoxy group, an ethoxy group, a propoxy group, an isopropoxy group, a 1,1-dimethylpropoxy group, a butoxy group, an isobutoxy group, a sec-butoxy group, a tert-butoxy group, an isopentyloxy group, a 1-methylbutoxy group, a 2-methylbutoxy group, an neopentyloxy group, a 1-ethylpropoxy group, an n-pentyloxy group, a hexyloxy group, a heptyloxy group, and an octyloxy group.

Specific examples of the cycloalkyloxy group having 3 to 6 carbon atoms for Q include a cyclopropyloxy group, a cyclobutyloxy group, a cyclopentyloxy group, and a cyclohexyloxy group.

Examples of the alkyl group having 1 to 2 carbon atoms substituted with the alkoxy group having 1 to 4 carbon atoms for Q include a methoxymethyl group, an ethoxymethyl group, an ethoxyethyl group, and a butoxymethyl group.

Specific examples of the alkylthio group substituted with the alkyl group having 1 to 4 carbon atoms for Q include a methylthiomethyl group, a methylthioethyl group, an ethylthiomethyl group, and a butylthiomethyl group.

Specific examples of the alkoxy group having 1 to 6 carbon atoms substituted with the acylamino group having 1 to 4 carbon atoms for Q include an acetylaminomethoxy group, a 2-(propionylamino)ethoxy group, a 3-(acetylamino)propoxy group, a 3-(propionylamino)propoxy group, a 3-(isopropionylamino)propoxy group, a 3-(butyroylamino)propoxy group, a 3-(isobutyroylamino)propoxy group, a 3-(sec-butyroylamino)propoxy group, a 3-(tert-butyroylamino)propoxy group, a 4-(acetylamino)butoxy group, a 5-(acetylamino)pentyloxy group, and a 6-(acetylamino)hexyloxy group.

Specific examples of the alkyl group having 1 to 6 carbon atoms substituted with the acylamino group having 1 to 4 carbon atoms for Q include an acetylaminomethyl group, a 2-(propionylamino)ethyl group, a 3-(acetylamino)propyl group, a 3-(propionylamino)propyl group, a 3-(isopropionylamino)propyl group, a 3-(butyroylamino)propyl group, a 3-(isobutyroylamino)propyl group, a 3-(sec-butyroylamino) propyl group, 3-(tert-butyroylamino)propyl group, a 4-(acetylamino)butyl group, a 5-(acetylamino)pentyl group, and a 6-(acetylamino)hexyl group.

Specific examples of the alkylamino group having 1 to 8 carbon atoms for Q include a methylamino group, an ethylamino group, a propylamino group, an isopropylamino group, a butylamino group, an isobutylamino group, a sec-butylamino group, a tert-butylamino group, a neopentylamino group, a 1-ethylpropylamino group, an n-pentylamino group, a hexylamino group, a heptylamino group, and an octylamino group.

Specific examples of the alkenyl group having 2 to 6 carbon atoms for Q include an allyl group, an isopropenyl group, a 1-butenyl group, a 2-butenyl group, a 2-pentenyl group, and a 5-hexenyl group.

Examples of the aralkyl group for Q include a benzyl group and a phenethyl group.

$X^1$ in the tetrazoylhydroxime compound represented by the general formula (6) represents a hydrogen atom, a halogen atom, an alkyl group, or an alkoxy group.

Examples of the halogen atom for $X^1$ include a chlorine atom, a bromine atom, an iodine atom, and a fluorine atom. Among these, chlorine or a fluorine atom is particularly preferable.

The alkyl group for $X^1$ is preferably an alkyl group having 1 to 4 carbon atoms and specific examples thereof include a methyl group, an ethyl group, an n-propyl group, an isopropyl group, a 1,1-dimethylpropyl group, an n-butyl group, an isobutyl group, a sec-butyl group, and a tert-butyl group. Among these groups, a methyl group is particularly preferable.

The alkoxy group for $X^1$ is preferably an alkoxy group having 1 to 3 carbon atoms and specific examples thereof include a methoxy group, an ethoxy group, a propoxy group, and an isopropoxy group. Among these groups, a methoxy group is particularly preferable.

$Y^1$ in the tetrazoylhydroxime compound represented by the general formula (6) represents an alkyl group. Among alkyl groups, an alkyl group having 1 to 3 carbon atoms such as a methyl group, an ethyl group, an n-propyl group, or an isopropyl group is preferable, and a methyl group is particularly preferable.

$X^2$ in the tetrazoylhydroxime compound represented by the general formula (7) represents an alkyl group, an alkoxy group, a cyano group, a methanesulfonyl group, a nitro group, a trifluoromethyl group, or an aryl group.

The alkyl group for $X^2$ is preferably an alkyl group having 1 to 4 carbon atoms, such as a methyl group, an ethyl group, an n-propyl group, an isopropyl group, a 1,1-dimethylpropyl group, an n-butyl group, an isobutyl group, a sec-butyl group, or a tert-butyl group. Among these alkyl groups, a methyl group or a tert-butyl group is particularly preferable.

The alkoxy group for $X^2$ is preferably an alkoxy group having 1 to 3 carbon atoms, such as a methoxy group, an ethoxy group, a propoxy group, or an isopropoxy group. Among these alkoxy groups, a methoxy group is particularly preferable.

Specific examples of the aryl group for $X^2$ include a phenyl group, a 4-methylphenyl group, and a 4-chlorophenyl group. Among these aryl groups, a phenyl group is particularly preferable.

The alkyl group for $Y^2$ is preferably an alkyl group having 1 to 3 carbon atoms, such as a methyl group, an ethyl group, an n-propyl group, or an isopropyl group. Among these alkyl groups, a methyl group is particularly preferable.

Among the compounds represented by the general formula (1), preferred is a tetrazoyloxime derivative wherein Z is a group represented by the general formula:

QC(=O)NH—

(wherein Q represents an alkyl group having 1 to 8 carbon atoms, or an alkoxyl group having 1 to 8 carbon atoms) and Het is a pyridyl group represented by the general formula (4) or a thiazoyl group represented by the general formula (5), and particularly preferred is a tetrazoyloxime derivative wherein X is a hydrogen atom or a halogen atom.

The stereostructure of the oxime moiety, which exists in the tetrazoyloxime derivative represented by the general formula (1) and the tetrazoylhydroxyimino derivative represented by the general formula (6) or (7) includes (E) or (Z) isomer, and these stereoisomers are included in the present invention. The synthesized product is usually obtained in the form of the (Z) isomer or a mixture of (E) and (Z) isomers, each of which can be isolated by separation and purification.

In the tetrazoyloxime derivative represented by the general formula (1), the (Z) isomer is particularly superior to the (E) isomer in plant disease controlling activity. However, both the (E) isomer and the (Z) isomer exist in a fixed ratio in the form of a mixture since the (Z) isomer is converted into the (E) isomer by light in a natural environment. The stable ratios of the (E) and (Z) isomers vary according to the type of compound.

Method

The tetrazoyloxime derivative represented by the general formula (1) can be prepared by the method (A) in the case in which a tetrazoyl group is a tetrazoyl group represented by the general formula (2), or can be prepared by the method (B) in the case in which a tetrazoyl group is a tetrazoyl group represented by the general formula (3). However, the method of preparing the tetrazoyloxime derivative of the present invention is not limited to these methods.

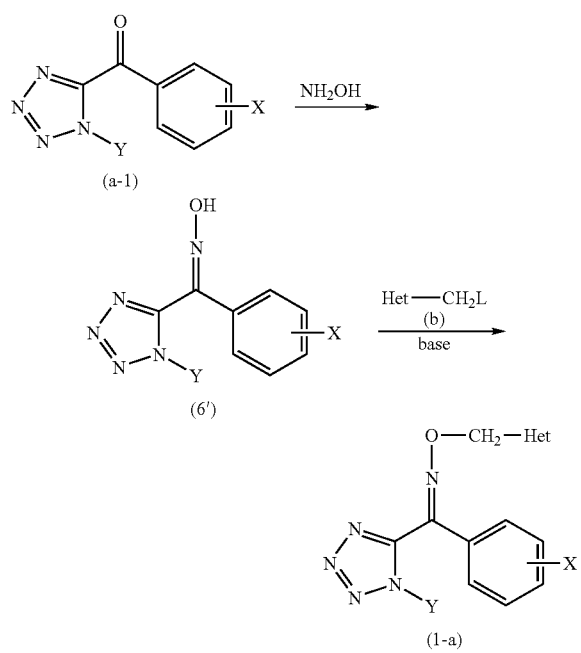

wherein X, Y and Het are as defined in the general formula (1), and L represents a chlorine atom, a bromine atom, or an iodine atom.

According to the method (A), a tetrazoyloxime derivative represented by the general formula (1-a) is prepared by reacting a tetrazoylmethanone derivative represented by the general formula (a-1) with hydroxylamine to obtain a tetrazoylhydroxyimino derivative represented by the general formula (6'), and reacting the tetrazoylhydroxyimino derivative with a compound represented by the general formula (b) in the presence of a base (for example, sodium hydride, sodium hydroxide, potassium hydroxide, sodium carbonate, potassium carbonate, cesium carbonate, triethylamine, pyridine, or N,N-dimethylaminopyridine).

The tetrazoylmethanone derivative represented by the general formula (a-1), as a starting material, can be easily prepared by reacting 1-alkyltetrazole with esters according to the method described, for example, in the document (Can. J. Chem., Vol. 49, page 2139, 1971).

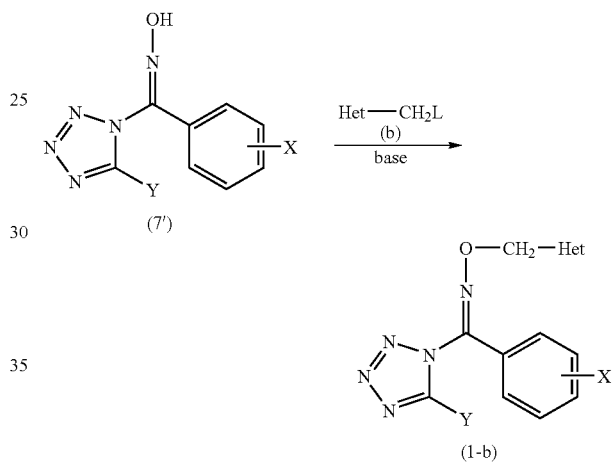

wherein X, Y and Het are as defined in the general formula (1), and L represents a chlorine atom, a bromine atom, or an iodine atom.

According to the method (B), a tetrazoyloxime derivative represented by the general formula (1-b) is prepared by reacting a tetrazoylhydroxyimino derivative represented by the general represented by the general formula (7') with a compound represented by the general formula (b) in the presence of a base (for example, sodium hydride, sodium hydroxide, potassium hydroxide, sodium carbonate, potassium carbonate, cesium carbonate, triethylamine, pyridine, or N,N-dimethylarminopyridine).

The tetrazoylhydroxyimino compound represented by the general formula (7'), as a starting material, can be easily prepared by reacting 5-alkyltetrazole with phenylhydroxyiminoyl chloride in the presence of triethylamine according to the method described, for example, in the document (Bull. Soc. Chim. Belg. Vol. 96, page 675, 1987).

Specific structures of the tetrazoyloxime derivative represented by the general formula (1) of the present invention prepared by the method described above are as shown in Tables 1 to 23. In the tables, X, Y, Z and R are as defined in the general formula (1), and the abbreviation cyclo denotes a ring structure.

TABLE 1

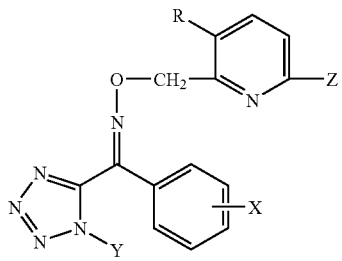

| Compound No. | Z | R | X | Y |
| --- | --- | --- | --- | --- |
| (1)-1 | H | H | H | CH$_3$ |
| (1)-2 | H$_2$N | H | H | CH$_3$ |
| (1)-3 | HCONH | H | H | CH$_3$ |
| (1)-4 | CH$_3$CONH | H | H | CH$_3$ |
| (1)-5 | CH$_3$CH$_2$CONH | H | H | CH$_3$ |
| (1)-6 | CH$_3$CH$_2$CH$_2$CONH | H | H | CH$_3$ |
| (1)-7 | (CH$_3$)$_2$CHCONH | H | H | CH$_3$ |
| (1)-8 | CH$_3$CH$_2$CH$_2$CH$_2$CONH | H | H | CH$_3$ |
| (1)-9 | (CH$_3$)$_2$CHCH$_2$CONH | H | H | CH$_3$ |
| (1)-10 | CH$_3$CH$_2$CH(CH$_3$)CONH | H | H | CH$_3$ |
| (1)-11 | (CH$_3$)$_3$CCONH | H | H | CH$_3$ |
| (1)-12 | CH$_3$CH$_2$CH$_2$CH$_2$CH$_2$CONH | H | H | CH$_3$ |
| (1)-13 | (CH$_3$)$_2$CHCH$_2$CH$_2$CONH | H | H | CH$_3$ |
| (1)-14 | CH$_3$CH$_2$CH(CH$_3$)CH$_2$CONH | H | H | CH$_3$ |
| (1)-15 | CH$_3$CH$_2$CH$_2$CH(CH$_3$)CONH | H | H | CH$_3$ |
| (1)-16 | (CH$_3$)$_3$CCH$_2$CONH | H | H | CH$_3$ |
| (1)-17 | (CH$_3$CH$_2$)$_2$CHCONH | H | H | CH$_3$ |
| (1)-18 | CH$_3$CH$_2$CH$_2$CH$_2$CH$_2$CH$_2$CONH | H | H | CH$_3$ |
| (1)-19 | CH$_3$CH$_2$CH$_2$CH$_2$CH$_2$CH$_2$CH$_2$CONH | H | H | CH$_3$ |
| (1)-20 | CH$_3$CH$_2$CH$_2$CH$_2$CH$_2$CH$_2$CH$_2$CH$_2$CONH | H | H | CH$_3$ |
| (1)-21 | cyclo-C$_3$H$_5$—CONH | H | H | CH$_3$ |
| (1)-22 | cyclo-C$_5$H$_9$—CONH | H | H | CH$_3$ |
| (1)-23 | cyclo-C$_6$H$_{11}$—CONH | H | H | CH$_3$ |

TABLE 2

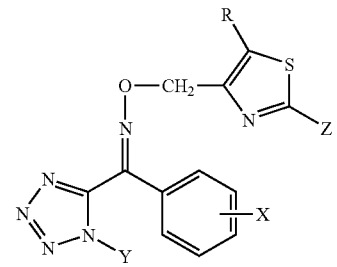

| Compound No. | Z | R | X | Y |
| --- | --- | --- | --- | --- |
| (2)-1 | H | H | H | CH$_3$ |
| (2)-2 | H$_2$N | H | H | CH$_3$ |
| (2)-3 | HCONH | H | H | CH$_3$ |
| (2)-4 | CH$_3$CONH | H | H | CH$_3$ |
| (2)-5 | CH$_3$CH$_2$CONH | H | H | CH$_3$ |
| (2)-6 | CH$_3$CH$_2$CH$_2$CONH | H | H | CH$_3$ |
| (2)-7 | (CH$_3$)$_2$CHCONH | H | H | CH$_3$ |
| (2)-8 | CH$_3$CH$_2$CH$_2$CH$_2$CONH | H | H | CH$_3$ |
| (2)-9 | (CH$_3$)$_2$CHCH$_2$CONH | H | H | CH$_3$ |
| (2)-10 | CH$_3$CH$_2$CH(CH$_3$)CONH | H | H | CH$_3$ |
| (2)-11 | (CH$_3$)$_3$CCONH | H | H | CH$_3$ |
| (2)-12 | CH$_3$CH$_2$CH$_2$CH$_2$CH$_2$CONH | H | H | CH$_3$ |
| (2)-13 | (CH$_3$)$_2$CHCH$_2$CH$_2$CONH | H | H | CH$_3$ |
| (2)-14 | CH$_3$CH$_2$CH(CH$_3$)CH$_2$CONH | H | H | CH$_3$ |
| (2)-15 | CH$_3$CH$_2$CH$_2$CH(CH$_3$)CONH | H | H | CH$_3$ |
| (2)-16 | (CH$_3$)$_3$CCH$_2$CONH | H | H | CH$_3$ |
| (2)-17 | (CH$_3$CH$_2$)$_2$CHCONH | H | H | CH$_3$ |
| (2)-18 | CH$_3$CH$_2$CH$_2$CH$_2$CH$_2$CH$_2$CONH | H | H | CH$_3$ |

TABLE 2-continued

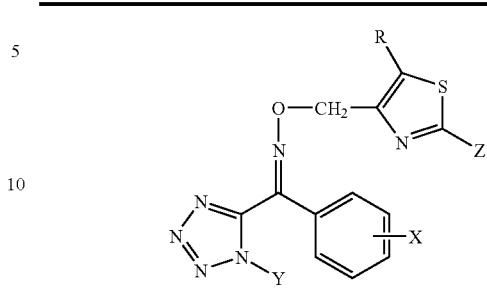

| Compound No. | Z | R | X | Y |
| --- | --- | --- | --- | --- |
| (2)-19 | CH$_3$CH$_2$CH$_2$CH$_2$CH$_2$CH$_2$CH$_2$CONH | H | H | CH$_3$ |
| (2)-20 | CH$_3$CH$_2$CH$_2$CH$_2$CH$_2$CH$_2$CH$_2$CH$_2$CONH | H | H | CH$_3$ |
| (2)-21 | cyclo-C$_3$H$_5$—CONH | H | H | CH$_3$ |
| (2)-22 | cyclo-C$_5$H$_9$—CONH | H | H | CH$_3$ |
| (2)-23 | cyclo-C$_6$H$_{11}$—CONH | H | H | CH$_3$ |

TABLE 3

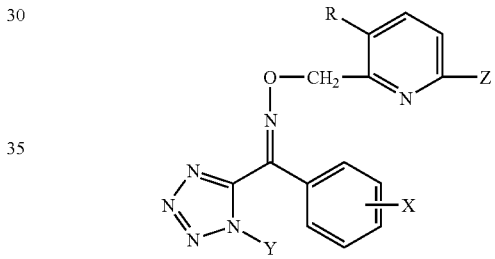

| Compound No. | Z | R | X | Y |
| --- | --- | --- | --- | --- |
| (3)-1 | CH$_3$OCONH | H | H | CH$_3$ |
| (3)-2 | CH$_3$CH$_2$OCONH | H | H | CH$_3$ |
| (3)-3 | CH$_3$CH$_2$CH$_2$OCONH | H | H | CH$_3$ |
| (3)-4 | (CH$_3$)$_2$CHOCONH | H | H | CH$_3$ |
| (3)-5 | CH$_3$CH$_2$CH$_2$CH$_2$OCONH | H | H | CH$_3$ |
| (3)-6 | (CH$_3$)$_2$CHCH$_2$OCONH | H | H | CH$_3$ |
| (3)-7 | CH$_3$CH$_2$CH(CH$_3$)OCONH | H | H | CH$_3$ |
| (3)-8 | (CH$_3$)$_3$COCONH | H | H | CH$_3$ |
| (3)-9 | CH$_3$CH$_2$CH$_2$CH$_2$CH$_2$OCONH | H | H | CH$_3$ |
| (3)-10 | (CH$_3$)$_2$CHCH$_2$CH$_2$OCONH | H | H | CH$_3$ |
| (3)-11 | CH$_3$CH$_2$CH(CH$_3$)CH$_2$OCONH | H | H | CH$_3$ |
| (3)-12 | CH$_3$CH$_2$CH$_2$CH(CH$_3$)OCONH | H | H | CH$_3$ |
| (3)-13 | (CH$_3$)$_3$CCH$_2$OCONH | H | H | CH$_3$ |
| (3)-14 | (CH$_3$CH$_2$)$_2$CHOCONH | H | H | CH$_3$ |
| (3)-15 | CH$_3$CH$_2$CH$_2$CH$_2$CH$_2$CH$_2$OCONH | H | H | CH$_3$ |
| (3)-16 | CH$_3$CH$_2$CH$_2$CH$_2$CH$_2$CH$_2$CH$_2$OCONH | H | H | CH$_3$ |
| (3)-17 | CH$_3$CH$_2$CH$_2$CH$_2$CH$_2$CH$_2$CH$_2$CH$_2$OCONH | H | H | CH$_3$ |
| (3)-18 | C$_6$H$_5$CH$_2$OCONH | H | H | CH$_3$ |
| (3)-19 | C$_6$H$_5$CH$_2$OCONH | H | H | CH$_3$ |
| (3)-20 | cyclo-C$_3$H$_5$—OCONH | H | H | CH$_3$ |
| (3)-21 | CH$_3$CH$_2$C(CH$_3$)$_2$OCONH | H | H | CH$_3$ |
| (3)-22 | cyclo-C$_5$H$_9$—OCONH | H | H | CH$_3$ |
| (3)-23 | cyclo-C$_6$H$_{11}$—OCONH | H | H | CH$_3$ |
| (3)-24 | CH$_3$CONHCH$_2$CH$_2$OCONH | H | H | CH$_3$ |
| (3)-25 | CH$_3$CONHCH$_2$CH$_2$CH$_2$OCONH | H | H | CH$_3$ |

TABLE 4

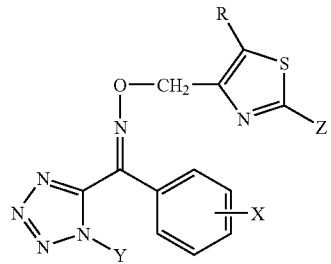

| Compound No. | Z | R | X | Y |
|---|---|---|---|---|
| (4)-1 | CH$_3$OCONH | H | H | CH$_3$ |
| (4)-2 | CH$_3$CH$_2$OCONH | H | H | CH$_3$ |
| (4)-3 | CH$_3$CH$_2$CH$_2$OCONH | H | H | CH$_3$ |
| (4)-4 | (CH$_3$)$_2$CHOCONH | H | H | CH$_3$ |
| (4)-5 | CH$_3$CH$_2$CH$_2$CH$_2$OCONH | H | H | CH$_3$ |
| (4)-6 | (CH$_3$)$_2$CHCH$_2$OCONH | H | H | CH$_3$ |
| (4)-7 | CH$_3$CH$_2$CH(CH$_3$)OCONH | H | H | CH$_3$ |
| (4)-8 | (CH$_3$)$_3$COCONH | H | H | CH$_3$ |
| (4)-9 | CH$_3$CH$_2$CH$_2$CH$_2$CH$_2$OCONH | H | H | CH$_3$ |
| (4)-10 | (CH$_3$)$_2$CHCH$_2$CH$_2$OCONH | H | H | CH$_3$ |
| (4)-11 | CH$_3$CH$_2$CH(CH$_3$)CH$_2$OCONH | H | H | CH$_3$ |
| (4)-12 | CH$_3$CH$_2$CH$_2$CH(CH$_3$)OCONH | H | H | CH$_3$ |
| (4)-13 | (CH$_3$)$_3$CCH$_2$OCONH | H | H | CH$_3$ |
| (4)-14 | (CH$_3$CH$_2$)$_2$CHOCONH | H | H | CH$_3$ |
| (4)-15 | CH$_3$CH$_2$CH$_2$CH$_2$CH$_2$CH$_2$OCONH | H | H | CH$_3$ |
| (4)-16 | CH$_3$CH$_2$CH$_2$CH$_2$CH$_2$CH$_2$CH$_2$OCONH | H | H | CH$_3$ |
| (4)-17 | CH$_3$CH$_2$CH$_2$CH$_2$CH$_2$CH$_2$CH$_2$CH$_2$OCONH | H | H | CH$_3$ |
| (4)-18 | C$_6$H$_5$CH$_2$OCONH | H | H | CH$_3$ |
| (4)-19 | C$_6$H$_5$CH$_2$CH$_2$OCONH | H | H | CH$_3$ |
| (4)-20 | cyclo-C$_3$H$_5$—OCONH | H | H | CH$_3$ |
| (4)-21 | CH$_3$CONHCH$_2$CH$_2$OCONH | H | H | CH$_3$ |
| (4)-22 | CH$_3$CONHCH$_2$CH$_2$CH$_2$OCONH | H | H | CH$_3$ |

TABLE 5

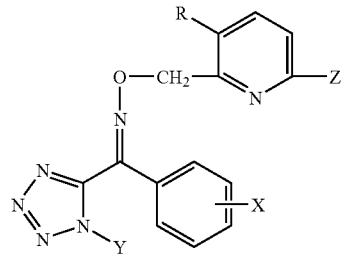

| Compound No. | Z | R | X | Y |
|---|---|---|---|---|
| (5)-1 | CH$_3$OCH$_2$CONH | H | H | CH$_3$ |
| (5)-2 | CH$_3$CH$_2$OCH$_2$CONH | H | H | CH$_3$ |
| (5)-3 | CH$_3$CH$_2$OCH$_2$CH$_2$CONH | H | H | CH$_3$ |
| (5)-4 | CH$_3$CH$_2$CH$_2$CH$_2$OCH$_2$CONH | H | H | CH$_3$ |
| (5)-5 | CH$_3$SCH$_2$CONH | H | H | CH$_3$ |
| (5)-6 | CH$_3$SCH$_2$CH$_2$CONH | H | H | CH$_3$ |
| (5)-7 | CH$_3$C(=CH$_2$)CONH | H | H | CH$_3$ |
| (5)-8 | CH$_3$CH=CHCH$_2$CH$_2$CONH | H | H | CH$_3$ |
| (5)-9 | CH$_3$CH$_2$CH=CHCH$_2$CONH | H | H | CH$_3$ |
| (5)-10 | CH$_3$CH$_2$CH=CHCONH | H | H | CH$_3$ |
| (5)-11 | CH$_3$CH$_2$CH$_2$CH=CHCONH | H | H | CH$_3$ |
| (5)-12 | C$_6$H$_5$CH$_2$CONH | H | H | CH$_3$ |

TABLE 5-continued

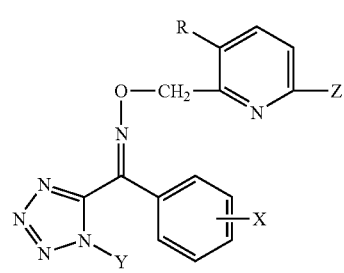

| Compound No. | Z | R | X | Y |
|---|---|---|---|---|
| (5)-13 | C$_6$H$_5$CH$_2$CH$_2$CONH | H | H | CH$_3$ |
| (5)-14 | C$_6$H$_5$CONH | H | H | CH$_3$ |
| (5)-15 | ClCH$_2$CONH | H | H | CH$_3$ |
| (5)-16 | F$_2$CHCONH | H | H | CH$_3$ |
| (5)-17 | F$_3$CCONH | H | H | CH$_3$ |
| (5)-18 | F$_3$CCH$_2$CONH | H | H | CH$_3$ |
| (5)-19 | CH$_3$CONHCH$_2$CH$_2$CONH | H | H | CH$_3$ |
| (5)-20 | CH$_3$CONHCH$_2$CH$_2$CH$_2$CH$_2$CH$_2$CONH | H | H | CH$_3$ |

TABLE 6

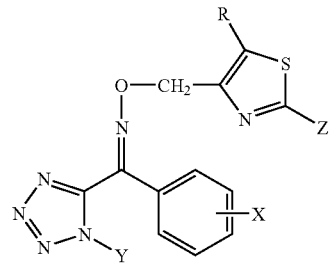

| Compound No. | Z | R | X | Y |
|---|---|---|---|---|
| (6)-1 | CH$_3$OCH$_2$CONH | H | H | CH$_3$ |
| (6)-2 | CH$_3$CH$_2$OCH$_2$CONH | H | H | CH$_3$ |
| (6)-3 | CH$_3$CH$_2$OCH$_2$CH$_2$CONH | H | H | CH$_3$ |
| (6)-4 | CH$_3$CH$_2$CH$_2$CH$_2$OCH$_2$CONH | H | H | CH$_3$ |
| (6)-5 | CH$_3$SCH$_2$CONH | H | H | CH$_3$ |
| (6)-6 | CH$_3$SCH$_2$CH$_2$CONH | H | H | CH$_3$ |
| (6)-7 | CH$_3$C(=CH$_2$)CONH | H | H | CH$_3$ |
| (6)-8 | CH$_3$CH=CHCH$_2$CH$_2$CONH | H | H | CH$_3$ |
| (6)-9 | CH$_3$CH$_2$CH=CHCH$_2$CONH | H | H | CH$_3$ |
| (6)-10 | CH$_3$CH$_2$CH=CHCONH | H | H | CH$_3$ |
| (6)-11 | CH$_3$CH$_2$CH$_2$CH=CHCONH | H | H | CH$_3$ |
| (6)-12 | C$_6$H$_5$CH$_2$CONH | H | H | CH$_3$ |
| (6)-13 | C$_6$H$_5$CH$_2$CH$_2$CONH | H | H | CH$_3$ |
| (6)-14 | C$_6$H$_5$CONH | H | H | CH$_3$ |
| (6)-15 | CH$_3$CH$_2$CH$_2$OCH$_2$CH$_2$CONH | H | H | CH$_3$ |
| (6)-16 | CH$_3$OCH$_2$CH$_2$OCONH | H | H | CH$_3$ |
| (6)-17 | F$_2$CHCONH | H | H | CH$_3$ |
| (6)-18 | F$_3$CCONH | H | H | CH$_3$ |
| (6)-19 | F$_3$CCH$_2$CONH | H | H | CH$_3$ |
| (6)-20 | CH$_3$CONHCH$_2$CH$_2$CONH | H | H | CH$_3$ |
| (6)-21 | CH$_3$CONHCH$_2$CH$_2$CH$_2$CH$_2$CH$_2$CONH | H | H | CH$_3$ |

TABLE 7

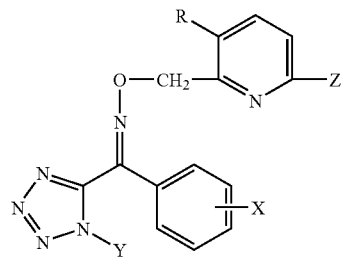

| Compound No. | Z | R | X | Y |
|---|---|---|---|---|
| (7)-1 | CH₃CH₂CH₂CONH | H | 4-Cl | CH₃ |
| (7)-2 | (CH₃)₂CHCONH | H | 4-Cl | CH₃ |
| (7)-3 | cyclo-C₃H₅—CONH | H | 4-Cl | CH₃ |
| (7)-4 | CH₃CH₂CONH | H | 3-F | CH₃ |
| (7)-5 | (CH₃)₂CHCONH | H | 3-F | CH₃ |
| (7)-6 | cyclo-C₃H₅—CONH | H | 3-F | CH₃ |
| (7)-7 | (CH₃)₃CCONH | H | 3-F | CH₃ |
| (7)-8 | (CH₃)₂CHCONH | H | 4-F | CH₃ |
| (7)-9 | (CH₃)₂CHCONH | H | 4-CH₃O | CH₃ |
| (7)-10 | (CH₃)₃CCONH | H | 4-CH₃O | CH₃ |
| (7)-11 | cyclo-C₃H₅—CONH | H | 4-CH₃O | CH₃ |
| (7)-12 | CH₃CH₂CH₂CH₂CONH | H | 4-CH₃ | CH₃ |
| (7)-13 | (CH₃)₃CCH₂CONH | H | 4-CH₃ | CH₃ |
| (7)-14 | (CH₃)₂CHCONH | Cl | H | CH₃ |
| (7)-15 | (CH₃)₂CHCONH | Cl | H | CH₃CH₂ |
| (7)-16 | (CH₃)₃CCONH | H | H | CH₃CH₂ |
| (7)-17 | (CH₃)₂CHCONH | H | H | CH₃CH₂ |
| (7)-18 | H | H | 4-F | CH₃ |
| (7)-19 | H | H | 3-F | CH₃ |
| (7)-20 | H | H | 4-Cl | CH₃ |

TABLE 8

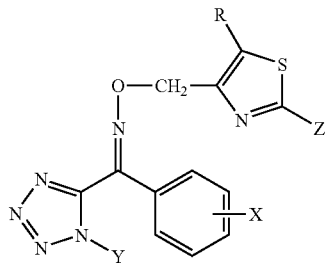

| Compound No. | Z | R | X | Y |
|---|---|---|---|---|
| (8)-1 | CH₃CH₂CH₂CONH | H | 4-Cl | CH₃ |
| (8)-2 | (CH₃)₂CHCONH | H | 4-Cl | CH₃ |
| (8)-3 | cyclo-C₃H₅—CONH | H | 4-Cl | CH₃ |
| (8)-4 | CH₃CH₂CONH | H | 3-F | CH₃ |
| (8)-5 | (CH₃)₂CHCONH | H | 3-F | CH₃ |
| (8)-6 | cyclo-C₃H₅—CONH | H | 3-F | CH₃ |
| (8)-7 | (CH₃)₃CCONH | H | 3-F | CH₃ |
| (8)-8 | (CH₃)₂CHCONH | H | 4-F | CH₃ |
| (8)-9 | (CH₃)₂CHCONH | H | 4-CH₃O | CH₃ |
| (8)-10 | (CH₃)₃CCONH | H | 4-CH₃O | CH₃ |
| (8)-11 | cyclo-C₃H₅—CONH | H | 4-CH₃O | CH₃ |
| (8)-12 | CH₃CH₂CH₂CH₂CONH | H | 4-CH₃ | CH₃ |
| (8)-13 | (CH₃)₃CCH₂CONH | H | 4-CH₃ | CH₃ |
| (8)-14 | (CH₃)₂CHCONH | Cl | H | CH₃ |
| (8)-15 | (CH₃)₂CHCONH | Cl | H | CH₃CH₂ |
| (8)-16 | (CH₃)₃CCONH | H | H | CH₃CH₂ |
| (8)-17 | (CH₃)₃CCONH | H | 4-Cl | CH₃ |

TABLE 9

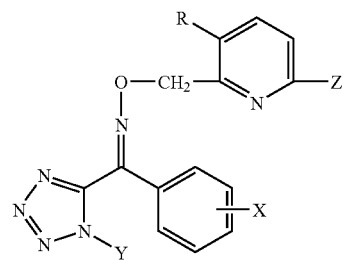

| Compound No. | Z | R | X | Y |
|---|---|---|---|---|
| (9)-1 | (CH₃)₃COCONH | H | 3-F | CH₃ |
| (9)-2 | (CH₃)₂CHOCONH | H | 4-F | CH₃ |
| (9)-3 | (CH₃)₃COCONH | H | 4-F | CH₃ |
| (9)-4 | (CH₃)₃COCONH | H | 4-CH₃ | CH₃ |
| (9)-5 | CH₃CH₂CH₂CH₂CH₂OCONH | H | 4-CH₃ | CH₃ |
| (9)-6 | CH₃CH₂CH₂OCONH | H | 3-F | CH₃ |
| (9)-7 | CH₃CH₂CH₂CH₂CH₂CONH | H | 3-CH₃ | CH₃ |
| (9)-8 | (CH₃)₃COCONH | H | 3-CH₃ | CH₃ |
| (9)-9 | CH₃CH₂C(CH₃)₂OCONH | H | 4-CH₃ | CH₃ |
| (9)-10 | CH₃CH₂CH₂CH₂CH₂OCONH | H | 2-CH₃ | CH₃ |
| (9)-11 | CH₃CH₂CH₂CH₂OCONH | H | 2-CH₃ | CH₃ |

TABLE 10

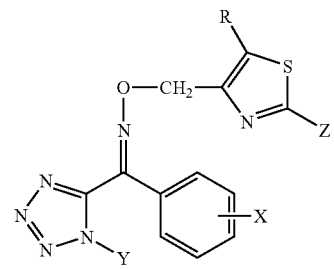

| Compound No. | Z | R | X | Y |
|---|---|---|---|---|
| (10)-1 | (CH₃)₃COCONH | H | 3-F | CH₃ |
| (10)-2 | (CH₃)₂CHOCONH | H | 4-F | CH₃ |
| (10)-3 | (CH₃)₃COCONH | H | 4-F | CH₃ |
| (10)-4 | (CH₃)₃COCONH | H | 4-CH₃ | CH₃ |
| (10)-5 | CH₃CH₂CH₂CH₂CH₂OCONH | H | 4-CH₃ | CH₃ |

TABLE 11

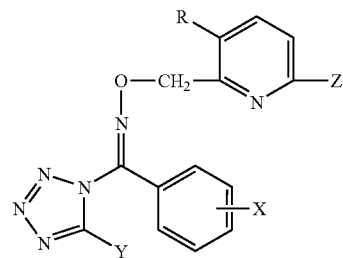

| Compound No. | Z | R | X | Y |
|---|---|---|---|---|
| (11)-1 | H | H | H | CH₃ |
| (11)-2 | H₂H | H | H | CH₃ |
| (11)-3 | HCONH | H | H | CH₃ |

TABLE 11-continued

Structure: pyridine ring with R at 3-position, Z at 6-position, connected via O-CH₂-N=C(tetrazole-Y)(phenyl-X)

| Compound No. | Z | R | X | Y |
|---|---|---|---|---|
| (11)-4 | CH₃CONH | H | H | CH₃ |
| (11)-5 | CH₃CH₂CONH | H | H | CH₃ |
| (11)-6 | CH₃CH₂CH₂CONH | H | H | CH₃ |
| (11)-7 | (CH₃)₂CHCONH | H | H | CH₃ |
| (11)-8 | CH₃CH₂CH₂CH₂CONH | H | H | CH₃ |
| (11)-9 | (CH₃)₂CHCH₂CONH | H | H | CH₃ |
| (11)-10 | CH₃CH₂CH(CH₃)CONH | H | H | CH₃ |
| (11)-11 | (CH₃)₃CCONH | H | H | CH₃ |
| (11)-12 | CH₃CH₂CH₂CH₂CH₂CONH | H | H | CH₃ |
| (11)-13 | (CH₃)₂CHCH₂CH₂CONH | H | H | CH₃ |
| (11)-14 | CH₃CH₂CH(CH₃)CH₂CONH | H | H | CH₃ |
| (11)-15 | CH₃CH₂CH₂CH(CH₃)CONH | H | H | CH₃ |
| (11)-16 | (CH₃)₃CCH₂CONH | H | H | CH₃ |
| (11)-17 | (CH₃CH₂)₂CHCONH | H | H | CH₃ |
| (11)-18 | CH₃CH₂CH₂CH₂CH₂CH₂CONH | H | H | CH₃ |
| (11)-19 | CH₃CH₂CH₂CH₂CH₂CH₂CH₂CONH | H | H | CH₃ |
| (11)-20 | CH₃CH₂CH₂CH₂CH₂CH₂CH₂CH₂CONH | H | H | CH₃ |
| (11)-21 | cyclo-C₃H₅-CONH | H | H | CH₃ |
| (11)-22 | cyclo-C₅H₉-CONH | H | H | CH₃ |
| (11)-23 | cyclo-C₆H₁₁-CONH | H | H | CH₃ |
| (11)-24 | CH₃CONHCH₂CH₂CONH | H | H | CH₃ |
| (11)-25 | CH₃CONHCH₂CH₂CH₂CH₂CH₂CONH | H | H | CH₃ |

TABLE 12

Structure: thiazole ring with R at 5-position, Z at 2-position, connected via O-CH₂-N=C(tetrazole-Y)(phenyl-X)

| Compound No. | Z | R | X | Y |
|---|---|---|---|---|
| (12)-1 | H | H | H | CH₃ |
| (12)-2 | H₂H | H | H | CH₃ |
| (12)-3 | HCONH | H | H | CH₃ |
| (12)-4 | CH₃CONH | H | H | CH₃ |
| (12)-5 | CH₃CH₂CONH | H | H | CH₃ |
| (12)-6 | CH₃CH₂CH₂CONH | H | H | CH₃ |
| (12)-7 | (CH₃)₂CHCONH | H | H | CH₃ |
| (12)-8 | CH₃CH₂CH₂CH₂CONH | H | H | CH₃ |
| (12)-9 | (CH₃)₂CHCH₂CONH | H | H | CH₃ |
| (12)-10 | CH₃CH₂CH(CH₃)CONH | H | H | CH₃ |
| (12)-11 | (CH₃)₃CCONH | H | H | CH₃ |
| (12)-12 | CH₃CH₂CH₂CH₂CH₂CONH | H | H | CH₃ |
| (12)-13 | (CH₃)₂CHCH₂CH₂CONH | H | H | CH₃ |
| (12)-14 | CH₃CH₂CH(CH₃)CH₂CONH | H | H | CH₃ |
| (12)-15 | CH₃CH₂CH₂CH(CH₃)CONH | H | H | CH₃ |

TABLE 12-continued

| Compound No. | Z | R | X | Y |
|---|---|---|---|---|
| (12)-16 | (CH₃)₃CCH₂CONH | H | H | CH₃ |
| (12)-17 | (CH₃CH₂)₂CHCONH | H | H | CH₃ |
| (12)-18 | CH₃CH₂CH₂CH₂CH₂CH₂CONH | H | H | CH₃ |
| (12)-19 | CH₃CH₂CH₂CH₂CH₂CH₂CH₂CONH | H | H | CH₃ |
| (12)-20 | CH₃CH₂CH₂CH₂CH₂CH₂CH₂CH₂CONH | H | H | CH₃ |
| (12)-21 | cyclo-C₃H₅-CONH | H | H | CH₃ |
| (12)-22 | cyclo-C₅H₉-CONH | H | H | CH₃ |
| (12)-23 | cyclo-C₆H₁₂-CONH | H | H | CH₃ |
| (12)-24 | CH₃CONHCH₂CH₂CONH | H | H | CH₃ |
| (12)-25 | CH₃CONHCH₂CH₂CH₂CH₂CH₂CONH | H | H | CH₃ |

TABLE 13

Structure: pyridine ring with R at 3-position, Z at 6-position, connected via O-CH₂-N=C(tetrazole-Y)(phenyl-X)

| Compound No. | Z | R | X | Y |
|---|---|---|---|---|
| (13)-1 | CH₃OCOCONH | H | H | CH₃ |
| (13)-2 | CH₃CH₂OCOCONH | H | H | CH₃ |
| (13)-3 | CH₃CH₂CH₂OCOCONH | H | H | CH₃ |
| (13)-4 | (CH₃)₂CHOCONH | H | H | CH₃ |
| (13)-5 | CH₃CH₂CH₂CH₂OCONH | H | H | CH₃ |
| (13)-6 | (CH₃)₂CHCH₂OCONH | H | H | CH₃ |
| (13)-7 | CH₃CH₂CH(CH₃)OCONH | H | H | CH₃ |
| (13)-8 | (CH₃)₃COCONH | H | H | CH₃ |
| (13)-9 | CH₃CH₂CH₂CH₂CH₂OCONH | H | H | CH₃ |
| (13)-10 | (CH₃)₂CHCH₂CH₂OCONH | H | H | CH₃ |
| (13)-11 | CH₃CH₂CH(CH₃)CH₂OCONH | H | H | CH₃ |
| (13)-12 | CH₃CH₂CH₂CH(CH₃)OCONH | H | H | CH₃ |
| (13)-13 | (CH₃)₃CCH₂OCONH | H | H | CH₃ |
| (13)-14 | (CH₃CH₂)₂CHOCONH | H | H | CH₃ |
| (13)-15 | CH₃CH₂CH₂CH₂CH₂CH₂OCONH | H | H | CH₃ |
| (13)-16 | CH₃CH₂CH₂CH₂CH₂CH₂CH₂OCONH | H | H | CH₃ |
| (13)-17 | CH₃CH₂CH₂CH₂CH₂CH₂CH₂CH₂OCONH | H | H | CH₃ |
| (13)-18 | C₆H₅CH₂OCONH | H | H | CH₃ |
| (13)-19 | C₆H₅CH₂OCONH | H | H | CH₃ |
| (13)-20 | cyclo-C₃H₅-OCONH | H | H | CH₃ |
| (13)-21 | cyclo-C₅H₉-OCONH | H | H | CH₃ |
| (13)-22 | cyclo-C₆H₁₁-OCONH | H | H | CH₃ |
| (13)-23 | CH₃CONHCH₂CH₂OCONH | H | H | CH₃ |
| (13)-24 | CH₃CONHCH₂CH₂CH₂CH₂OCONH | H | H | CH₃ |

TABLE 14

| Compound No. | Z | R | X | Y |
|---|---|---|---|---|
| (14)-1 | CH$_3$OCOCONH | H | H | CH$_3$ |
| (14)-2 | CH$_3$CH$_2$OCOCONH | H | H | CH$_3$ |
| (14)-3 | CH$_3$CH$_2$CH$_2$OCOCONH | H | H | CH$_3$ |
| (14)-4 | (CH$_3$)$_2$CHOCONH | H | H | CH$_3$ |
| (14)-5 | CH$_3$CH$_2$CH$_2$CH$_2$OCONH | H | H | CH$_3$ |
| (14)-6 | (CH$_3$)$_2$CHCH$_2$OCONH | H | H | CH$_3$ |
| (14)-7 | CH$_3$CH$_2$CH(CH$_3$)OCONH | H | H | CH$_3$ |
| (14)-8 | (CH$_3$)$_3$COCONH | H | H | CH$_3$ |
| (14)-9 | CH$_3$CH$_2$CH$_2$CH$_2$CH$_2$OCONH | H | H | CH$_3$ |
| (14)-10 | (CH$_3$)$_2$CHCH$_2$CH$_2$OCONH | H | H | CH$_3$ |
| (14)-11 | CH$_3$CH$_2$CH(CH$_3$)CH$_2$OCONH | H | H | CH$_3$ |
| (14)-12 | CH$_3$CH$_2$CH$_2$CH(CH$_3$)OCONH | H | H | CH$_3$ |
| (14)-13 | (CH$_3$)$_3$CCH$_2$OCONH | H | H | CH$_3$ |
| (14)-14 | (CH$_3$CH$_2$)$_2$CHOCONH | H | H | CH$_3$ |
| (14)-15 | CH$_3$CH$_2$CH$_2$CH$_2$CH$_2$CH$_2$OCONH | H | H | CH$_3$ |
| (14)-16 | CH$_3$CH$_2$CH$_2$CH$_2$CH$_2$CH$_2$CH$_2$OCONH | H | H | CH$_3$ |
| (14)-17 | CH$_3$CH$_2$CH$_2$CH$_2$CH$_2$CH$_2$CH$_2$CH$_2$OCONH | H | H | CH$_3$ |
| (14)-18 | C$_6$H$_5$CH$_2$OCONH | H | H | CH$_3$ |
| (14)-19 | C$_6$H$_5$CH$_2$CH$_2$OCONH | H | H | CH$_3$ |
| (14)-20 | cyclo-C$_3$H$_5$-OCONH | H | H | CH$_3$ |
| (14)-21 | CH$_3$CONHCH$_2$CH$_2$OCONH | H | H | CH$_3$ |
| (14)-22 | CH$_3$CONHCH$_2$CH$_2$CH$_2$OCONH | H | H | CH$_3$ |

TABLE 15

| Compound No. | Z | R | X | Y |
|---|---|---|---|---|
| (15)-1 | C$_6$H$_5$CH$_2$CONH | H | H | CH$_3$ |
| (15)-2 | C$_6$H$_5$CH$_2$CH$_2$CONH | H | H | CH$_3$ |
| (15)-3 | C$_6$H$_5$CONH | H | H | CH$_3$ |
| (15)-4 | F$_2$CHCONH | H | H | CH$_3$ |
| (15)-5 | F$_3$CCONH | H | H | CH$_3$ |
| (15)-6 | F$_3$CCH$_2$CH$_2$CONH | H | H | CH$_3$ |

TABLE 16

| Compound No. | Z | R | X | Y |
|---|---|---|---|---|
| (16)-1 | C$_6$H$_5$CH$_2$CONH | H | H | CH$_3$ |
| (16)-2 | C$_6$H$_5$CH$_2$CH$_2$CONH | H | H | CH$_3$ |
| (16)-3 | C$_6$H$_5$CONH | H | H | CH$_3$ |
| (16)-4 | F$_2$CHCONH | H | H | CH$_3$ |
| (16)-5 | F$_3$CCONH | H | H | CH$_3$ |
| (16)-6 | F$_3$CCH$_2$CH$_2$CONH | H | H | CH$_3$ |

TABLE 17

| Compound No. | Z | R | X | Y |
|---|---|---|---|---|
| (17)-1 | CH$_3$CH$_2$CH$_2$CONH | H | 4-Cl | CH$_3$ |
| (17)-2 | (CH$_3$)$_2$CHCONH | H | 4-Cl | CH$_3$ |
| (17)-3 | cyclo-C$_3$H$_5$-CONH | H | 4-Cl | CH$_3$ |
| (17)-4 | CH$_3$CH$_2$CONH | H | 3-F | CH$_3$ |
| (17)-5 | (CH$_3$)$_2$CHCONH | H | 3-F | CH$_3$ |
| (17)-6 | cyclo-C$_3$H$_5$-CONH | H | 3-F | CH$_3$ |
| (17)-7 | (CH$_3$)$_3$CCONH | H | 3-F | CH$_3$ |
| (17)-8 | (CH$_3$)$_2$CHCONH | H | 4-F | CH$_3$ |
| (17)-9 | (CH$_3$)$_2$CHCONH | H | 4-CH$_3$O | CH$_3$ |
| (17)-10 | (CH$_3$)$_3$CCONH | H | 4-CH$_3$O | CH$_3$ |
| (17)-11 | cyclo-C$_3$H$_5$-CONH | H | 4-CH$_3$O | CH$_3$ |
| (17)-12 | CH$_3$CH$_2$CH$_2$CH$_2$CH$_2$CONH | H | 4-CH$_3$ | CH$_3$ |
| (17)-13 | (CH$_3$)$_3$CCH$_2$CONH | H | 4-CH$_3$ | CH$_3$ |
| (17)-14 | (CH$_3$)$_2$CHCONH | Cl | H | CH$_3$ |
| (17)-15 | (CH$_3$)$_2$CHCONH | Cl | H | CH$_3$CH$_2$ |
| (17)-16 | (CH$_3$)$_3$CCONH | H | H | CH$_3$CH$_2$ |
| (17)-17 | (CH$_3$)$_2$CHCONH | H | H | CH$_3$CH$_2$ |
| (17)-18 | H | H | 4-F | CH$_3$ |
| (17)-19 | H | H | 3-F | CH$_3$ |
| (17)-20 | H | H | 4-Cl | CH$_3$ |
| (17)-21 | CH$_3$CH$_2$CH$_2$CH$_2$CH$_2$CONH | H | H | CH$_3$CH$_2$ |

TABLE 18

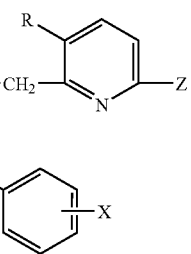

| Compound No. | Z | R | X | Y |
|---|---|---|---|---|
| (18)-1 | CH$_3$CH$_2$CH$_2$CONH | H | 4-Cl | CH$_3$ |
| (18)-2 | (CH$_3$)$_2$CHCONH | H | 4-Cl | CH$_3$ |
| (18)-3 | cyclo-C$_3$H$_5$-CONH | H | 4-Cl | CH$_3$ |
| (18)-4 | CH$_3$CH$_2$CONH | H | 3-F | CH$_3$ |
| (18)-5 | (CH$_3$)$_2$CHCONH | H | 3-F | CH$_3$ |
| (18)-6 | cyclo-C$_3$H$_5$-CONH | H | 3-F | CH$_3$ |
| (18)-7 | (CH$_3$)$_3$CCONH | H | 3-F | CH$_3$ |
| (18)-8 | (CH$_3$)$_2$CHCONH | H | 4-F | CH$_3$ |
| (18)-9 | (CH$_3$)$_2$CHCONH | H | 4-CH$_3$O | CH$_3$ |
| (18)-10 | (CH$_3$)$_3$CCONH | H | 4-CH$_3$O | CH$_3$ |
| (18)-11 | cyclo-C$_3$H$_5$-CONH | H | 4-CH$_3$O | CH$_3$ |
| (18)-12 | CH$_3$CH$_2$CH$_2$CH$_2$CONH | H | 4-CH$_3$ | CH$_3$ |
| (18)-13 | (CH$_3$)$_3$CCH$_2$CONH | H | 4-CH$_3$ | CH$_3$ |
| (18)-14 | (CH$_3$)$_2$CHCONH | Cl | H | CH$_3$ |
| (18)-15 | (CH$_3$)$_2$CHCONH | Cl | H | CH$_3$CH$_2$ |
| (18)-16 | (CH$_3$)$_3$CCONH | H | H | CH$_3$CH$_2$ |
| (18)-17 | (CH$_3$)$_2$CHCONH | H | H | CH$_3$ |
| (18)-18 | CH$_3$CH$_2$CH$_2$CONH | H | 4-Cl | CH$_3$ |
| (18)-19 | CH$_3$CH$_2$CH$_2$CH$_2$CONH | H | H | CH$_3$CH$_2$ |

TABLE 19

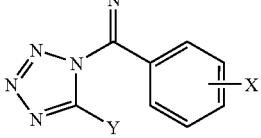

| Compound No. | Z | R | X | Y |
|---|---|---|---|---|
| (19)-1 | (CH$_3$)$_3$COCONH | H | 3-F | CH$_3$ |
| (19)-2 | (CH$_3$)$_2$CHOCONH | H | 4-F | CH$_3$ |
| (19)-3 | (CH$_3$)$_3$COCONH | H | 4-F | CH$_3$ |
| (19)-4 | (CH$_3$)$_3$COCONH | H | 4-CH$_3$ | CH$_3$ |
| (19)-5 | CH$_3$CH$_2$CH$_2$OCONH | H | 3-F | CH$_3$ |
| (19)-6 | CH$_3$CH$_2$CH$_2$OCONH | H | 4-F | CH$_3$ |
| (19)-7 | CH$_3$CH$_2$CH$_2$OCONH | H | 3-Cl | CH$_3$ |
| (19)-8 | CH$_3$CH$_2$CH$_2$OCONH | H | 4-Cl | CH$_3$ |
| (19)-9 | CH$_3$CH$_2$CH$_2$OCONH | H | 3-CH$_3$ | CH$_3$ |
| (19)-10 | CH$_3$CH$_2$CH$_2$OCONH | H | 4-CH$_3$ | CH$_3$ |
| (19)-11 | CH$_3$CH$_2$CH$_2$CH$_2$OCONH | H | 3-F | CH$_3$ |
| (19)-12 | CH$_3$CH$_2$CH$_2$CH$_2$OCONH | H | 4-F | CH$_3$ |
| (19)-13 | CH$_3$CH$_2$CH$_2$CH$_2$OCONH | H | 3-Cl | CH$_3$ |
| (19)-14 | CH$_3$CH$_2$CH$_2$CH$_2$OCONH | H | 4-Cl | CH$_3$ |
| (19)-15 | CH$_3$CH$_2$CH$_2$CH$_2$OCONH | H | 3-CH$_3$ | CH$_3$ |

TABLE 19-continued

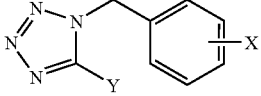

| Compound No. | Z | R | X | Y |
|---|---|---|---|---|
| (19)-16 | CH$_3$CH$_2$CH$_2$CH$_2$OCONH | H | 4-CH$_3$ | CH$_3$ |
| (19)-17 | CH$_3$CH$_2$CH$_2$CH$_2$CH$_2$OCONH | H | 3-F | CH$_3$ |
| (19)-18 | CH$_3$CH$_2$CH$_2$CH$_2$CH$_2$OCONH | H | 4-F | CH$_3$ |
| (19)-19 | CH$_3$CH$_2$CH$_2$CH$_2$CH$_2$OCONH | H | 3-Cl | CH$_3$ |
| (19)-20 | CH$_3$CH$_2$CH$_2$CH$_2$CH$_2$OCONH | H | 4-Cl | CH$_3$ |
| (19)-21 | CH$_3$CH$_2$CH$_2$CH$_2$CH$_2$OCONH | H | 3-CH$_3$ | CH$_3$ |
| (19)-22 | CH$_3$CH$_2$CH$_2$CH$_2$CH$_2$OCONH | H | 4-CH$_3$ | CH$_3$ |
| (19)-23 | CH$_3$CH$_2$CH$_2$CH$_2$OCONH | H | 4-CH$_3$O | CH$_3$ |
| (19)-24 | CH$_3$CH$_2$CH$_2$CH$_2$CH$_2$OCONH | H | 4-CH$_3$O | CH$_3$ |

TABLE 20

| Compound No. | Z | R | X | Y |
|---|---|---|---|---|
| (19)-25 | CH$_3$CH$_2$CH$_2$CH$_2$OCONH | H | 4-CN | CH$_3$ |
| (19)-26 | CH$_3$CH$_2$CH$_2$CH$_2$CH$_2$OCONH | H | 4-CN | CH$_3$ |
| (19)-27 | CH$_3$CH$_2$CH$_2$CH$_2$OCONH | H | 4-CH$_3$SO$_2$ | CH$_3$ |
| (19)-28 | CH$_3$CH$_2$CH$_2$CH$_2$CH$_2$OCONH | H | 4-CH$_3$SO$_2$ | CH$_3$ |
| (19)-29 | CH$_3$CH$_2$CH$_2$CH$_2$OCONH | H | 4-NO$_2$ | CH$_3$ |
| (19)-30 | CH$_3$CH$_2$CH$_2$CH$_2$CH$_2$OCONH | H | 4-NO$_2$ | CH$_3$ |
| (19)-31 | CH$_3$CH$_2$CH$_2$CH$_2$OCONH | H | 4-CF$_3$ | CH$_3$ |
| (19)-32 | CH$_3$CH$_2$CH$_2$CH$_2$CH$_2$OCONH | H | 4-CF$_3$ | CH$_3$ |
| (19)-33 | CH$_3$CH$_2$CH$_2$CH$_2$OCONH | H | H | CH$_3$ |
| (19)-34 | CH$_3$CH$_2$CH$_2$CH$_2$OCONH | H | 4-CH$_3$CH$_2$ | CH$_3$ |
| (19)-35 | CH$_3$CH$_2$CH$_2$CH$_2$OCONH | H | 4-(CH$_3$)$_3$C | CH$_3$ |
| (19)-36 | CH$_3$CH$_2$CH$_2$CH$_2$OCONH | H | 4-C$_6$H$_5$ | CH$_3$ |
| (19)-37 | CH$_3$CH$_2$CH$_2$CH$_2$OCONH | H | 2-Cl | CH$_3$ |
| (19)-38 | CH$_3$CH$_2$CH$_2$CH$_2$OCONH | H | 2-CH$_3$ | CH$_3$ |

TABLE 21

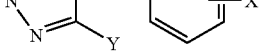

| Compound No. | Z | R | X | Y |
|---|---|---|---|---|
| (20)-1 | (CH$_3$)$_3$COCONH | H | 3-F | CH$_3$ |
| (20)-2 | (CH$_3$)$_2$CHOCONH | H | 4-F | CH$_3$ |
| (20)-3 | (CH$_3$)$_3$COCONH | H | 4-F | CH$_3$ |
| (20)-4 | (CH$_3$)$_3$COCONH | H | 4-CH$_3$ | CH$_3$ |
| (20)-5 | CH$_3$CH$_2$CH$_2$OCONH | H | 4-CH$_3$ | CH$_3$ |
| (20)-6 | CH$_3$CH$_2$CH$_2$CH$_2$OCONH | H | H | CH$_3$CH$_2$ |

TABLE 22

[Structure: pyridine ring with R substituent, O—CH2 linked to N=C bearing tetrazole (N-Y) and phenyl-X groups; Z on pyridine]

| Compound No. | Z | R | X | Y |
|---|---|---|---|---|
| (21)-1 | CH₃NHCONH | H | H | CH₃ |
| (21)-2 | CH₃CH₂NHCONH | H | H | CH₃ |
| (21)-3 | CH₃CH₂CH₂NHCONH | H | H | CH₃ |
| (21)-4 | (CH₃)₂CHNHCONH | H | H | CH₃ |
| (21)-5 | CH₃CH₂CH₂CH₂NHCONH | H | H | CH₃ |
| (21)-6 | (CH₃)₂CHCH₂NHCONH | H | H | CH₃ |
| (21)-7 | CH₃CH₂CH(CH₃)NHCONH | H | H | CH₃ |
| (21)-8 | (CH₃)₃CNHCONH | H | H | CH₃ |
| (21)-9 | CH₃CH₂CH₂CH₂CH₂CONH | H | H | CH₃ |
| (21)-10 | (CH₃)₂CHCH₂CH₂NHCONH | H | H | CH₃ |
| (21)-11 | CH₃CH₂CH(CH₃)CH₂CONH | H | H | CH₃ |
| (21)-12 | CH₃CH₂CH₂CH(CH₃)CONH | H | H | CH₃ |
| (21)-13 | (CH₃)₃CCH₂NHCONH | H | H | CH₃ |
| (21)-14 | (CH₃CH₂)₂CHNHCONH | H | H | CH₃ |
| (21)-15 | CH₃CH₂CH₂CH₂CH₂CH₂CONH | H | H | CH₃ |
| (21)-16 | CH₃CH₂CH₂CH₂CH₂CH₂CH₂CONH | H | H | CH₃ |
| (21)-17 | CH₃CH₂CH₂CH₂CH₂CH₂CH₂CH₂CONH | H | H | CH₃ |

TABLE 23

[Structure: similar pyridine/tetrazole/phenyl scaffold as Table 22]

| Compound No. | Z | R | X | Y |
|---|---|---|---|---|
| (21)-1 | CH₃NHCONH | H | H | CH₃ |
| (21)-2 | CH₃CH₂NHCONH | H | H | CH₃ |
| (21)-3 | CH₃CH₂CH₂NHCONH | H | H | CH₃ |
| (21)-4 | (CH₃)₂CHNHCONH | H | H | CH₃ |
| (21)-5 | CH₃CH₂CH₂CH₂NHCONH | H | H | CH₃ |
| (21)-6 | (CH₃)₂CHCH₂NHCONH | H | H | CH₃ |
| (21)-7 | CH₃CH₂CH(CH₃)NHCONH | H | H | CH₃ |
| (21)-8 | (CH₃)₃CNHCONH | H | H | CH₃ |
| (21)-9 | CH₃CH₂CH₂CH₂CH₂NHNHCONH | H | H | CH₃ |
| (21)-10 | (CH₃)₂CHCH₂CH₂NHCONH | H | H | CH₃ |
| (21)-11 | CH₃CH₂CH(CH₃)CH₂NHCONH | H | H | CH₃ |
| (21)-12 | CH₃CH₂CH₂CH(CH₃)NHCONH | H | H | CH₃ |
| (21)-13 | (CH₃)₃CCH₂NHCONH | H | H | CH₃ |
| (21)-14 | (CH₃CH₂)₂CHNHCONH | H | H | CH₃ |
| (21)-15 | CH₃CH₂CH₂CH₂CH₂CH₂NHCONH | H | H | CH₃ |
| (21)-16 | CH₃CH₂CH₂CH₂CH₂CH₂CH₂NHCONH | H | H | CH₃ |
| (21)-17 | CH₃CH₂CH₂CH₂CH₂CH₂CH₂CH₂NHCONH | H | H | CH₃ |

The tetrazoyloxime derivative of the present invention has high activity against various plant pathogens and exhibits high control effects for prevention and treatment of plant diseases caused by plant pathogens. The tetrazoyloxime derivative of the present invention is particularly effective for various plant diseases caused by filamentous fungi among plant pathogens, and is used particularly preferably to control various plant diseases caused by oomycetes, zygomycetes, ascomycetes, basidiomycetes, and deuteromycetes. Examples of plant pathogens include, but are not limited to, the following.

Examples of oomycetes include fungi belonging to the genus *Pythium*, such as damping-off (*Pythium ultimum*) on various crops; fungi belonging to the genus *Phytophthora*, such as late blight (*Phytophthora infestans*) on potato and phytophthora rot (*Phytophthora capsici*) on tomato; fungi belonging to the genus *Pseudoperonospora*, such as downy mildew (*Pseudoperonospora cubensis*) on cucumber and downy mildew (*Pseudoperonospora humuli*) on hops; fungi belonging to the genus *Plasmopara*, such as downy mildew (*Plasmopara viticola*) on grape; and fungi belonging to the genus *Peronospora*, such as downy mildew (*Peronospora brassicae*) on vegetables belonging to the family Cruciferae, downy mildew (*Peronospora destructor*) on leeks, and downy mildew (*Peronospora spinaciae*) on spinach.

Examples of ascomycetes include fungi belonging to the genus *Erysiphe*, such as powdery mildew (*Erysiphe graminis*) on wheat; fungi belonging to the genus *Sphaerotheca*, such as powdery mildew (*Sphaerotheca fuliginea*) on vegetables; fungi belonging to the genus *Venturia*, such as black spot (*Venturia inaequalis*) on apple and black spot (*Venturia nashicola*) on pear; fungi belonging to the genus *Pyrenophora*, such as net blotch (*Pyrenophora teres*) on barley; fungi belonging to the genus *Cochliobolus*, such as leaf spot (*Cochliobolus sativus*) on wheat; and fungi belonging to the genus *Sclerotinia*, such as sclerotal disease (*Sclerotinia sclerotiorum*) on vegetables.

Examples of basidiomycetes include fungi belonging to the genus *Puccinia*, such as leaf rust (*Puccinia recondita*) on wheat; fungi belonging to the genus *Tilletia*, such as bunt (*Tilletia caries*) on wheat; and fungi belonging to the genus *Ustilago*, such as head smut (*Ustilago nuda*) on barley.

Examples of deuteromycetes include fungi belonging to the genus *Phoma*, such as stem blight (*Phoma asparagi*) on asparagus; fungi belonging to the genus *Septoria*, such as glume blotch (*Septoria nodorum*) on wheat; fungi belonging to the genus *Colletotrichum*, such as anthracnose (*Colletotrichum lagenarium*) on gourds; fungi belonging to the genus *Pyricularia*, such as blast (*Pyricularia oryzae*) on rice; fungi belonging to the genus *Botrytis*, such as gray mold (*Botrytis cinerea*) on vegetables; fungi belonging to the genus *Alternaria*, such as alternaria blotch (*Alternaria mali*) on apple and ring spot (*Alternaria solani*) on tomato; fungi belonging to the genus *Cercospora*, such as brown spots (*Cercospora beticola*) on sugar beet; fungi belonging to the genus *Cladosporium*, such as black spot (*Cladosporium carpophilum*) on peach; and fungi belonging to the genus *Rhizoctonia*, such as sheath blight (*Rhizoctonia solani*) on rice.

Although the tetrazoyloxime derivative of the present invention can be used alone as an agricultural chemical, the tetrazoyloxime derivative, as an active ingredient, is usually mixed with conventional solid and liquid carriers used in the formulation of the agricultural chemical, and auxiliaries such as dispersants, diluents, emulsifiers, spreaders, and thickeners to give formulations in the form of wettable powders, liquid formulations, oil solutions, dusts, granules, and sols (flowables).

Examples of the solid and liquid carriers include talc, clay, bentonite, kaolin, diatomaceous earth, montmorillonite, mica, vermiculite, gypsum, calcium carbonate, white carbon, wood flour, starch, alumina, silicate, dextrin, waxes, alcohols (e.g., methyl alcohol, ethyl alcohol, n-propyl alcohol, isopropyl alcohol, n-butyl alcohol, ethylene glycol, etc.), petroleum fractions (e.g., petroleum ether, kerosine, solvent naphtha, etc.), aliphatic or alicyclic hydrocarbons (e.g., n-hexane, cyclohexane, etc.), aromatic hydrocarbons (e.g., benzene, toluene, xylene, ethylbenzene, chlorobenzene, cumene, methylnaphthalene, etc.), halogenated hydrocarbons (e.g., chloroform, dichloromethane, etc.), ethers (e.g., isopropyl ether, ethylene oxide, tetrahydrofuran, etc.), ketones (e.g., acetone, methyl ethyl ketone, cyclohexanone, methyl isobutyl ketone, etc.), esters (e.g., ethyl acetate, butyl acetate, ethylene glycol acetate, amyl acetate, etc.), acid amides (e.g., dimethylformamide, diethylacetanilide, etc.), nitriles (e.g., acetonitrile, propionitrile, acrylonitrile, etc.), sulfoxides (e.g., dimethyl sulfoxide, etc.), and alcohol ethers (e.g., ethylene glycol monomethyl ether, ethylene glycol monoethyl ether, etc.).

Examples of the auxiliary include nonionic surfactants (e.g., polyoxyethylene alkyl ether, polyoxyethylene alkyl ester, polyoxyethylene alkyl phenyl ether, polyoxyethylene sorbitan alkyl ester, sorbitan alkyl ester, etc.), anionic surfactants (e.g., alkylbenzene sulfonate, alkyl sulfosuccinate, polyoxyethylene alkyl sulfonate, aryl sulfonate, etc.), cationic surfactants (e.g., alkylamines, polyoxyethylene alkylamines, quaternary ammonium salts, etc.), amphoteric surfactants (e.g., alkylaminoethylglycine, alkyldimethylbetaine, etc.), polyvinyl alcohol, hydroxypropylcellulose, carboxymethylcellulose, gum arabic, tragacanth gum, xanthan gum, polyvinyl acetate, gelatin, casein, and sodium alginate.

The tetrazoyloxime derivative of the present invention can be mixed with agricultural chemicals such as publicly known conventional fungicides, herbicides, plant growth regulators, insecticides and acaricides, and fertilizers. The content of tetrazoyloxime derivative of the present invention varies according to the type of the formulation, the method of application, and other conditions, but is usually within a range from 0.5 to 95% by weight, and preferably from 2 to 70% by weight.

The method of applying the agricultural chemical of the present invention includes, for example, application to plants (stem and leaf application), application to growing soil of plants (soil application), application to the surface of the water in a paddy field (water surface application), and application to seeds (seed treatment).

The amount of the agricultural chemical of the present invention to be applied varies according to the kind of plant and the type of damage. In the case of the stem and leaf application, a solution containing an active ingredient in a concentration within a range of 1 to 10000 ppm, preferably from 10 to 1000 ppm, is preferably applied in an amount within a range from 50 to 300 liters per 10 ares. In the case of the soil application and water surface application, the active ingredient is preferably applied in an amount within a range from 0.1 to 1000 g, and particularly preferably from 10 to 100 g, per 10 ares. In the case of the seed treatment, the active ingredient is preferably applied in an amount within a range from 0.001 to 50 g per 1 kg of seeds.

EXAMPLES

The following Preparation Examples, Formulation Examples and Test Examples further illustrate the present invention, although the present invention is not limited to these Examples.

First, Preparation Examples of the tetrazoylhydroxyimino derivative are described.

Preparation Example 1

(1-methyltetrazol-5-yl)phenylmethanone (11.1 g, 59.1 mmol) and hydroxylammonium chloride (10.3 g, 148 mmol) were added to 100 ml of pyridine, followed by stirring at 45° C. for 24 hours. After the completion of the reaction, the reaction solution was concentrated under reduced pressure and water and ethyl acetate were added to the resulting residue, and then the reaction product was extracted. The organic layer was washed in turn with dilute hydrochloric acid, water and an aqueous sodium hydrogencarbonate, and the organic layer was dried over anhydrous magnesium sulfate. The solvent was distilled off from the organic layer to obtain (1-methyltetrazol-5-yl)phenylmethanoneoxime (12.0 g, yield: 100%) represented by the formua:

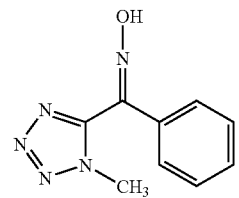

$^1$H-NMR(CDCl$_3$, δ): 4.03(s, 3H), 7.3–7.55(m, 5H), 9.0 (brd, 1H).

Preparation Example 2

In the same manner as in Preparation Example 1, except that (1-methyltetrazol-5-yl)4-chlorophenylmethanone (560 mg, 2.52 mmol) was used in place of (1-methyltetrazol-5-yl)phenylmethanone in Preparation Example 1, 600 mg of (1-methyltetrazol-5-yl)4-chlorophenylmethanoneoxime represented by the formula:

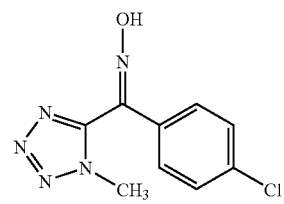

was obtained.

$^1$H-NMR(CDCl$_3$, δ): 4.04 (s, 3H), 7.36 (m, 2H), 7.46 (m, 2H), 9.00 (brd, 11H).

Preparation Example 3

In the same manner as in Preparation Example 1, except that (1-methyltetrazol-5-yl)3-fluorophenylmethanone (964 mg, 4.68 mmol) was used in place of (1-methyltetrazol-5-yl)phenylmethanone in Preparation Example 1, 999 mg of (1-methyltetrazol-5-yl)3-fluorophenylmethanoneoxime represented by the formula:

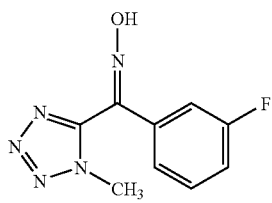

was obtained.

$^1$H-NMR (CDCl$_3$, δ): 4.04 (s, 3H), 7.11 (m, 1H), 7.2–7.5 (m, 3H), 12.31 (brd, 1H).

Preparation Example 4

In the same manner as in Preparation Example 1, except that (1-methyltetrazol-5-yl)4-fluorophenylmethanone (850 mg, 4.14 mmol) was used in place of (1-methyltetrazol-5-yl)phenylmethanone in Preparation Example 1, 930 mg of (1-methyltetrazol-5-yl)4-fluorophenylmethanoneoxime represented by the formula:

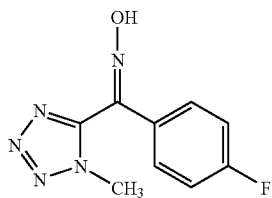

was obtained.

$^1$H-NMR (CDCl$_3$, δ): 4.05 (s, 3H), 7.08 (dd, 1H, J=8.6, 8.6 Hz), 7.53(m, 2H), 8.68 (brd, 1H).

Preparation Example 5

In the same manner as in Preparation Example 1, except that (1-methyltetrazol-5-yl)4-methoxyphenylmethanone (386 mg, 1.77 mmol) was used in place of (1-methyltetrazol-5-yl)phenylmethanone in Preparation Example 1, 410 mg of (1-methyltetrazol-5-yl)4-methoxyphenylmethanoneoxime represented by the formula:

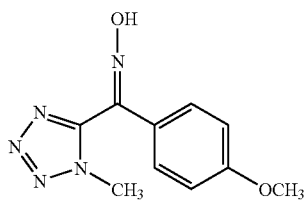

was obtained.

$^1$H-NMR (CDCl$_3$, δ): 3.83 (s, 3H), 4.03 (s, 3H), 6.89 (m, 2H), 7.45 (m, 2H), 8.36 (brd, 1H).

Preparation Example 6

In the same manner as in Preparation Example 1, except that (1-methyltetrazol-5-yl)3-methylphenylmethanone (1.36 g, 6.78 mmol) was used in place of (1-methyltetrazol-5-yl)phenylmethanone in Preparation Example 1, 1.31 g of 1-methyltetrazol-5-yl)3-methylphenylmethanoneoxime represented by the formula:

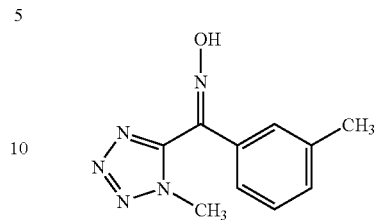

was obtained.

$^1$H-NMR (CDCl$_3$, δ): 2.31 (s, 3H), 3.99 (s, 3H), 7.2–7.3 (m, 5H), 9.92 (brd, 1H).

Preparation Example 7

In the same manner as in Preparation Example 1, except that (1-methyltetrazol-5-yl)4-methylphenylmethanone (1.65 g, 8.16 mmol) was used in place of (1-methyltetrazol-5-yl)phenylmethanone in Preparation Example 1, 1.67 g of (1-methyltetrazol-5-yl)4-methylphenylmethanoneoxime represented by the formula:

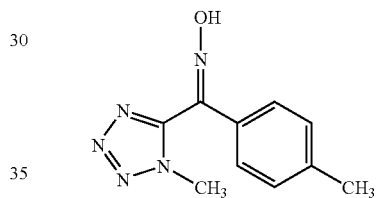

was obtained.

$^1$H-NMR (CDCl$_3$, δ): 2.37 (s, 3H), 4.01 (s, 3H), 7.18 (m, 2H), 7.37 (m, 2H), 9.02 (brd, 1H).

Preparation Example 8

In the same manner as in Preparation Example 1, except that (1-methyltetrazol-5-yl)2-methylphenylmethanone (1.90 g, 9.40 mmol) was used in place of (1-methyltetrazol-5-yl)phenylmethanone in Preparation Example 1, 1.93 g of (1-methyltetrazol-5-yl)2-methylphenylmethanoneoxime represented by the formula:

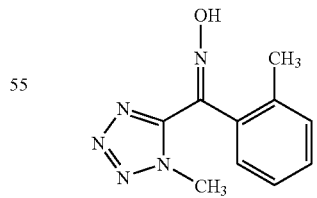

was obtained.

$^1$H-NMR (CDCl$_3$, δ):
Z isomer: 2.22 (s, 3H), 4.06 (s, 3H), 7.2–7.4 (m, 4H), 9.05(brd, 1H).
E isomer: 2.21 (s, 3H), 4.31 (s, 3H), 7.15–7.45 (m, 4H), 8.43 (brd, 1H).

Preparation Example 9

In the same manner as in Preparation Example 1, except that (1-ethyltetrazol-5-yl)phenylmethanone (1.00 g, 4.95 mmol) was used in place of (1-methyltetrazol-5-yl)phenylmethanone in Preparation Example 1, 1.00 g of (1-ethyltetrazol-5-yl)phenylmethanoneoxime represented by the formula:

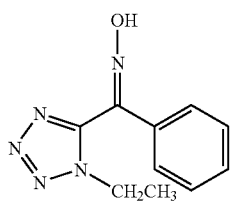

was obtained.
$^1$H-NMR (CDCl$_3$, δ): 1.51 (t, J=7.3 Hz, 3H), 4.35 (q, J=7.3 Hz, 2H), 7.33–7.55 (m, 5H), 10.45 (brd, 1H).

Preparation Example 10

To a solution prepared by dissolving 3-fluorobenzoaldoxime (2.78 g, 20 mmol) in 25 ml of N,N-dimethylformamide, imide N-chlorosuccinate (2.80 g, 21 mmol) was added while maintaining a liquid temperature at 45° C. or lower. After stirring at room temperature for one hour, the reaction solution was poured into saturated ammonium chloride water and then extracted with ethyl acetate. The organic layer was washed in turn with water and saturated saline solution, and the organic layer was dried over anhydrous sodium sulfate. The solvent was distilled off form the organic layer, and 5-methyltetrazole (1.70 g, 20 mmol) and 25 ml of dichloromethane were added to the resulting residue. To the solution, triethylamine (3.6 ml, 1.26 mmol) was added dropwise at room temperature. After stirring at room temperature for 6 hours, the reaction solution was poured into saturated ammonium chloride water and then extracted with ethyl acetate. The organic layer was washed in turn with water and saturated saline solution and then dried over anhydrous sodium sulfate. The solvent was distilled off and the resulting residue was purified by silica gel chromatography to obtain 1.40 g of (5-methyltetrazol-1-yl)-3-fluorophenylmethanoneoxime represented by the formula:

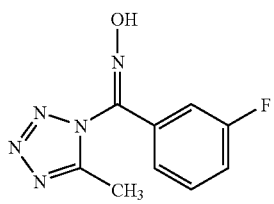

$^1$H-NMR (CDCl$_3$, δ): 2.57 (s, 3H), 7.06–7.09 (m, 1H), 7.18–7.27 (m, 2H), 7.36–7.43 (m, 1H), 8.67 (s, 1H).

Preparation Example 11

In the same manner as in Preparation Example 10, except that 4-fluorobenzoaldoxime (2.78 g, 20 mmol) was used in place of 3-fluorobenzoaldoxime in Preparation Example 10, 1.00 g of (5-methyltetrazol-1-yl)-4-fluorophenylmethanoneoxime represented by the formula:

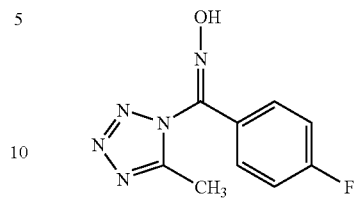

was obtained.
$^1$H-NMR (CDCl$_3$, δ): 2.53 (s, 3H), 7.06–7.12 (m, 2H), 7.38–7.45 (m, 2H), 12.11 (s, 1H).

Preparation Example 12

In the same manner as in Preparation Example 10, except that 3-chlorobenzoaldoxime (3.11 g, 20 mmol) was used in place of 3-fluorobenzoaldoxime in Preparation Example 10, 2.05 g of (5-methyltetrazol-1-yl)-3-chlorophenylmethanoneoxime represented by the formula:

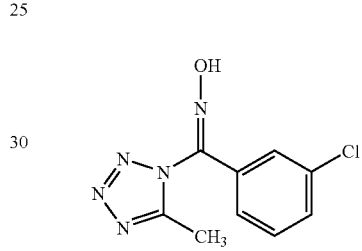

was obtained.
$^1$H-NMR (CDCl$_3$, δ): 2.58 (s, 3H), 7.20–7.23 (m, 1H), 7.33–7.38 (m, 2H), 7.46–7.51 (m,1H), 9.22 (s, 1H).

Preparation Example 13

In the same manner as in Preparation Example 10, except that 4-chlorobenzoaldoxime (3.11 g, 20 mmol) was used in place of 3-fluorobenzoaldoxime in Preparation Example 10, 2.17 g of (5-methyltetrazol-1-yl)-4-chlorophenylmethanoneoxime represented by the formula:

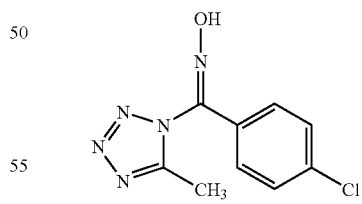

was obtained.
$^1$H-NMR (CDCl$_3$, δ): 2.53 (s, 3H), 7.33–7.39 (m, 4H), 12.07 (s, 1H).

Preparation Example 14

In the same manner as in Preparation Example 10, except that 4-methylbenzoaldoxime (2.70 g, 20 mmol) was used in place of 3-fluorobenzoaldoxime in Preparation Example 10, 2.50 g of (5-methyltetrazol-1-yl)-4-methylphenylmethanoneoxime represented by the formula:

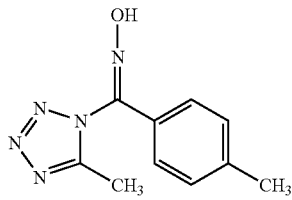

was obtained.

¹H-NMR (CDCl₃, δ): 2.39 (s, 3H), 2.56 (s, 3H), 7.20–7.30 (m, 4H), 8.69 (s, 1H).

Preparation Example 15

In the same manner as in Preparation Example 10, except that 4-methoxybenzoaldoxime (3.20 g, 20 mmol) was used in place of 3-fluorobenzoaldoxime in Preparation Example 10, 1.96 g of (5-methyltetrazol-1-yl)-4-methoxyphenylmethanoneoxime represented by the formula:

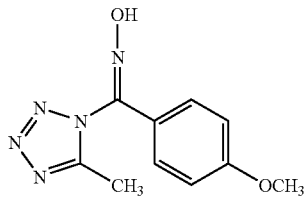

was obtained.

¹H-NMR (CDCl₃, δ): 2.55 (s, 3H), 3.84 (s, 3H), 6.89–6.94 (m, 2H), 7.30–7.35 (m, 2H), 8.13 (s, 1H).

Preparation Example 16

In the same manner as in Preparation Example 10, except that 4-cyanobenzoaldoxime (2.92 g, 20 mmol) was used in place of 3-fluorobenzoaldoxime in Preparation Example 10, 1.70 g of 5-methyltetrazol-1-yl)-4-cyanophenylmethanoneoxime represented by the formula:

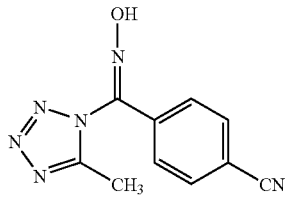

was obtained.

¹H-NMR (CDCl₃, δ): 2.54 (s, 3H), 7.53–7.56 (m, 2H), 7.68–7.71 (m, 2H), 12.71 (s, 1H).

Preparation Example 17

In the same manner as in Preparation Example 10, except that 4-methylsulfonylbenzoaldoxime (1.30 g, 6.5 mmol) was used in place of 3-fluorobenzoaldoxime in Preparation Example 10, 1.20 g of (5-methyltetrazol-1-yl)-4-methylsulfonylphenylmethanoneoxime represented by the formula:

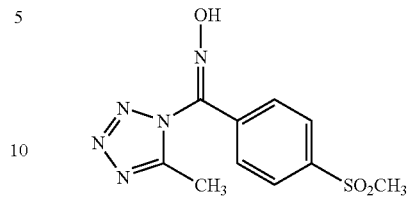

was obtained.

¹H-NMR (CDCl₃, δ): 2.55 (s, 3H), 3.08 (s, 3H), 7.62–7.65 (m, 2H), 7.95–7.98 (m, 2H), 12.68 (s, 1H).

Preparation Example 18

In the same manner as in Preparation Example 10, except that 4-nitrobenzoaldoxime (3.32 g, 20 mmol) was used in place of 3-fluorobenzoaldoxime in Preparation Example 10, 1.00 g of (5-methyltetrazol-1-yl)-4-nitrophenylmethanoneoxime represented by the formula:

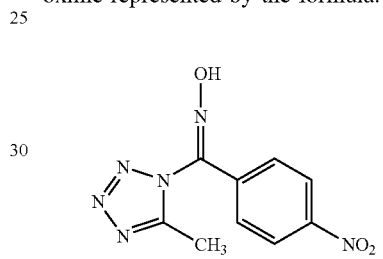

was obtained.

¹H-NMR (CDCl₃, δ): 2.55 (s, 3H), 7.61–7.64 (m, 2H), 8.24–8.26 (m, 2H), 12.72 (s, 1H).

Preparation Example 19

In the same manner as in Preparation Example 10, except that 4-trifluoromethylbenzoaldoxime (3.78 g, 20 mmol) was used in place of 3-fluorobenzoaldoxime in Preparation Example 10, 0.78 g of (5-methyltetrazol-1-yl)-4-trifluoromethylphenylmethanoneoxime represented by the formula:

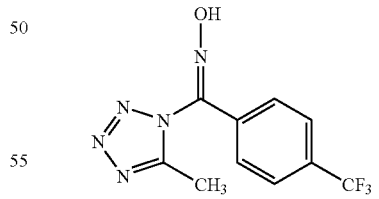

was obtained.

¹HNMR (CDCl₃, δ): 2.54 (s, 3H), 7.55 (d, 2H, J=8.41 Hz), 7.66 (d, 2H, J=8.41 Hz), 12.26 (s, 1H).

Preparation Example 20

In the same manner as in Preparation Example 10, except that 4-ethylbenzoaldoxime (1.49 g, 10 mmol) was used in place of 3-fluorobenzoaldoxime in Preparation Example 10, 1.35 g of (5-methyltetrazol-1-yl)-4-ethylphenylmethanone-oxime represented by the formula:

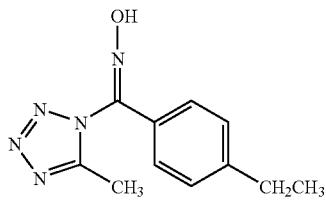

was obtained.

$^1$H-NMR (CDCl$_3$, δ): 1.34 (t, 3H, J=7.51 Hz), 2.56 (s, 3H), 2.69 (q, 2H, J=7.69H), 7.22–7.32 (4H, m), 8.69 (s, 1H).

Preparation Example 21

In the same manner as in Preparation Example 10, except that 4-tert-butylbenzoaldoxime (1.77 g, 10 mmol) was used in place of 3-fluorobenzoaldoxime in Preparation Example 10, 1.35 g of (5-methyltetrazol-1-yl)-4-tert-butylphenyl-methanoneoxime represented by the formula:

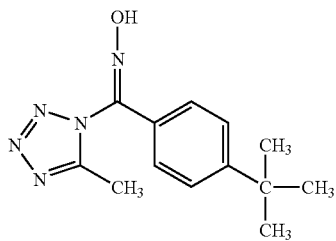

was obtained.

$^1$H-NMR (CDCl$_3$, δ): 1.33 (s, 9H), 2.55 (s, 3H), 7.32 (d, 2H, J=8.62 Hz), 7.44 (d, 2H, J=8.62 Hz), 7.99 (s, 1H).

Preparation Example 22

In the same manner as in Preparation Example 10, except that 4-biphenylaldoxime (1.97 g, 20 mmol) was used in place of 3-fluorobenzoaldoxime in Preparation Example 10, 1.20 g of 5-methyltetrazol-1-yl)-4-biphenylmethanone-oxime represented by the formula:

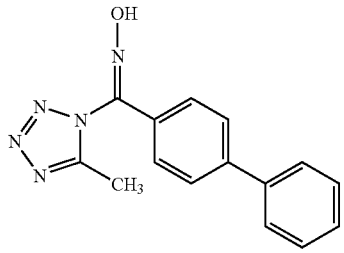

was obtained.

$^1$H-NMR (CDCl$_3$, δ): 2.56 (s, 3H), 7.29–7.49 (m, 5H), 7.58–7.63 (m, 4H), 12.05 (s, 1H).

Preparation Example 23

In the same manner as in Preparation Example 10, except that 5-ethyltetrazole (2.00 g, 20.4 mmol) was used in place of 5-methyltetrazole and benzaldoxime (2.70 g, 22 mmol) was used in place of 3-fluorobenzoaldoxime in Preparation Example 10, 1.93 g of (5-ethyltetrazol-1-yl)phenylmetha-noneoxime represented by the formula:

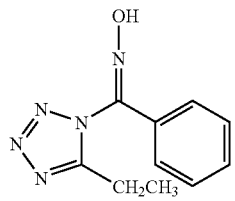

was obtained.

$^1$H-NMR (CDCl$_3$, δ): 1.37 (t, J=7.6 Hz, 3H), 2.88 (q, J=7.6 Hz, 2H), 7.35–7.55 (m, 5H), 9.42 (s, 1H).

Preparation Examples of a tetrazoyloxime derivative are described below.

Preparation Example 24

After sodium hydride (1.40 g, 60% in oil) was suspended in 30 ml of dry N,N-dimethylformamide, a solution of (1-methyltetrazol-5-yl)phenylmethanoneoxime (2.6 g, 12.6 mmol) obtained in Preparation Example 1 and 15 ml of dry N,N-dimethylformamide was added dropwise while cooling in an ice bath. After continuously stirring for 10 minutes, a solution prepared by dissolving 2-bromomethyl-6-(hex-anoylamino)pyridine (4.0 g, 14 mmol) in 15 ml of dry N,N-dimethylformamide was added dropwise. After the completion of dropwise addition, the ice bath was removed and the mixture was continuously stirred for 1.5 hours. The reaction solution was poured into saturated ammonium chloride water, and the reaction product was extracted with ethyl acetate. The organic layer was washed in turn with water and saturated saline solution, and the organic layer was dried over anhydrous sodium sulfate. The solvent was distilled off from the organic layer and the resulting residue was purified by silica gel chromatography to obtain 3.55 g of (Z)-(1-methyltetrazol-5-yl)phenylmethanoneoxime 0-(6-(hexanoylamino)pyridin-2-yl)methyloxime (compound No. (1)-12) represented by the formula:

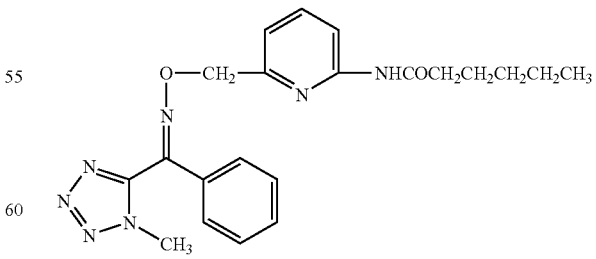

$^1$H-NMR (CDCl$_3$, δ): 0.91 (t, 3H, J=7.2 Hz), 1.37 (m, 4H), 1.74 (m, 2H), 2.39 (t, 2H, J=7.7 Hz), 3.97 (s, 3H), 5.26 (s, 2H), 7.00 (d, 1H, J=7.3 Hz), 7.3–7.55 (m, 5H), 7.70 (dd, 1H, J=7.3, 8.1 Hz), 7.86 (brd, 1H), 8.15 (d, 1H, J=8.1 Hz).

Preparation Example 25

(1-methyltetrazol-5-yl)phenylmethanoneoxime (60 mg, 0.30 mmol) obtained in Preparation Example 1 and 4-chloromethyl-2-(n-pentyloxycarbonylamino)thiazole (85 mg, 0.32 mmol) were dissolved in 4 ml of dry N,N-dimethylformamide, and sodium hydride (40 mg, 60% in oil) was added to the solution while cooling in an ice bath. After the ice bath was removed and the mixture was continuously stirred for 3 hours, the reaction solution was poured into saturated ammonium chloride water and the reaction product was extracted with ethyl acetate. The organic layer was washed in turn with water and saturated saline solution, and then the organic layer was dried over anhydrous magnesium sulfate. The solvent was distilled off from the organic layer, and the resulting residue was purified by silica gel chromatography to obtain 120 mg of (Z)-(1-methyltetrazol-5-yl)phenylmethanoneoxime 0-(2-(n-pentyloxycarbonylamino)thiazol-4-yl)methyloxime (compound No. (4)-9) represented by the formula:

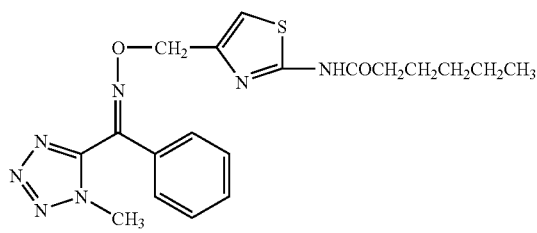

$^1$H-NMR (CDCl$_3$): 0.89 (t, 3H, J=7.0 Hz), 1.34 (m, 4H), 1.68 (m, 2H), 3.87 (s, 3H), 4.23 (t, 2H, J=6.9 Hz), 5.30 (s, 2H), 6.89 (s, 1H), 7.30–7.55 (m, 5H), 10.21 (brd, 1H).

Preparation Example 26

Sodium hydride (1.79 g, 60% oily product) was suspended in 60 ml of dry N,N-dimethylformamide and a solution of (Z)-(5-methyltetrazol-1-yl)phenylmethanoneoxime (8.24 g, 40.6 mmol) and 30 ml of dry N,N-dimethylformamide was added dropwise to the suspension while cooling in an ice bath. After stirring continuously for 10 minutes, a solution of 2-bromomethyl-6-(hexanoylamino)pyridine (12.7 g, 44.5 mmol) and 40 ml of dry N,N-dimethylformamide was added dropwise. After the completion of dropwise addition, the ice bath was removed and the mixture was continuously stirred for 2 hours. The reaction solution was poured into saturated ammonium chloride water and the reaction product was extracted with ethyl acetate. The organic layer was washed in turn with water and saturated saline solution, and then the organic layer was dried over anhydrous sodium sulfate. The solvent was distilled off from the organic layer, and the resulting residue was purified by silica gel chromatography to obtain 10.5 g of (Z)-(5-methyltetrazol-1-yl)phenylmethanoneoxime 0-(6-(hexanoylamino)pyridin-2-yl)methyloxime (compound No. (11)-12) represented by the formula:

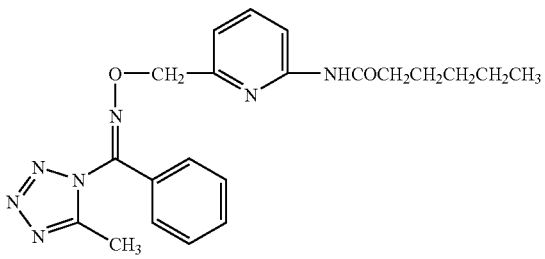

$^1$H-NMR (CDCl$_3$, δ): 0.91 (t, 3H, J=7.1 Hz), 1.31–1.38 (m, 4H), 1.70–1.77 (m, 2H), 2.45 (t, 2H, J=7.5 Hz), 2.46 (s, 3H), 5.23 (s, 2H), 6.92 (s, 1H), 7.34–7.53 (m, 5H), 9.10 (brd, 1H).

Preparation Example 27

(Z)-(5-methyltetrazol-1-yl)phenylmethanoneoxime (100 mg, 0.42 mmol) and 4-chloromethyl-2-(n-hexanoylamino)thiazole (120 mg, 0.51 mmol) were dissolved in 2 ml of dry N,N-dimethylformamide, and sodium hydride (40 mg, 60% in oil) was added to the solution while cooling in an ice bath. After removing the ice bath, the mixture was continuously stirred for 3 hours. The reaction solution was poured into saturated ammonium chloride water and the reaction product was extracted with ethyl acetate. The organic layer was washed in turn with water and saturated saline solution, and then the organic layer was dried over anhydrous magnesium sulfate. The solvent was distilled off from the organic layer and the resulting residue was purified by silica gel chromatography to obtain 117 mg of (Z)-(5-methyltetrazol-1-yl)phenylmethanoneoxime 0-(2-(n-hexanoylamino)thiazol-4-yl)methyloxime (Compound No. (12)-12) represented by the formula:

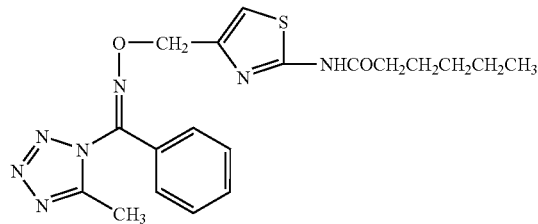

$^1$H-NMR (CDCl$_3$): 0.91 (t, 3H, J=7.1 Hz), 1.31–1.38 (m, 4H), 1.70–1.77 (m, 2H), 2.45 (t, J=7.5 Hz, 2H), 2.46 (s, 3H), 5.23 (s, 2H), 6.92 (s, 1H), 7.34–7.53 (m, 5H), 9.10 (brd, 1H).

$^1$NMR spectrum data of tetrazoyloxime derivatives prepared in the same manner as in these Preparation Examples are summarized in Tables 24 to 45. Regarding the indication of the compounds in the tables, for example, the compound (1)-1-represents a compound No. 1 in Table 1. "Z/E" in the column represents a (Z) isomer or an (E) isomer.

TABLE 24

| Compound No. | Z/E | $^1$H-NMR (CDCl$_3$) δ |
|---|---|---|
| (1)-1 | Z | 4.00(s, 3H), 5.41(s, 1H), 7.22–7.28(m, 2H), 7.3–7.47(m, 3H), 7.51–7.55(m, 2H), 7.67(t, d, J=7.7Hz, J=1.7Hz. 1H), 8.58(d, d, J=7.5Hz, J=1, 7Hz, 1H). |
| (1)-2 | Z | 3.4(s, 3H), 5.25(s, 2H), 7.15(d, J=7.1Hz, 1H), 7.35–7.53(m, 5H), 7.80(d, d, J=7.1Hz, J=8.0Hz, 1H), 8.10(d, J=8.0Hz. 1H). |
| (1)-5 | Z | 1.26(t, J=7.5Hz, 3H), 2.44(q, J=7.5Hz, 2H), 4.10(s, 3H), 5.27(s, 2H), 7.00(d, J=7.5Hz, 1H), 7.35–7.52(m, 5H), 7.70(d, d, J=7.5Hz, J=8.1Hz, 1H), 8.14(d, J=8.1Hz, 1H). |
| (1)-7 | Z | 1.27(d, 6H, J=7.0Hz), 2.55(seq, 1H, J=7.0Hz), 3.97(s, 3H), 5.27(s, 2H), 6.99(d, 1H, J=7.5Hz), 7.3–7.55(m, 5H), 7.70(dd, 1H, J=7.5, 8.4Hz), 7.85(brd, 1H), 8.17(d, 1H, J=8.4Hz). |
| (1)-8 | Z | 0.93(t, J=7.3Hz, 3H), 1.40(sept, J=7.3Hz, 2H), 1.72(sept, 7.3Hz, 2H), 2.41(t, J=7.3Hz, 2H), 3.97(s, 3H), 5.26(s, 2H), 7.00(d, J=7.5Hz, 1H), 7.35–7.52(m, 5H), 7.70(d, J=7.5Hz, J=8.2Hz, 1H), 8.16(d, J=8.2Hz. 1H). |
| (1)-11 | Z | 1.34(s, 9H), 3.98(s, 3H), 5.27(s, 2H), 7.00(d, J=6.8Hz, 1H), 7.35–7.53(m, 5H), 7.72(d, d, J=6.8Hz, J=8.2Hz, 1H), 8.18(d, J=8.2Hz, 1H). |

TABLE 25

| Compound No. | Z/E | $^1$H-NMR (CDCl$_3$) δ |
|---|---|---|
| (1)-12 | Z | 0.91(t, J=6.9Hz, 3H), 1.33–1.41(m, 3H), 1.69–1.79(m, 3H), 2.3(t, J=7.2Hz, 2H), 3.98(s, 3H), 5.26(s, 2H), 7.00(d, J=7.0Hz, 1H), 7.35–7.52(m, 5H), 7.69(d, d, J=7.0Hz, J=8.3Hz, 1H), 8.15(d, J=8.3Hz, 1H). |
| (1)-16 | Z | 1.11(s, 9H), 2.26(s, 2H), 3.97(s, 3H), 5.26(s, 2H), 7.00(d, 1H, J=7.5Hz), 7.3–7.55(m, 5H), 7.69(dd, 1H, J=7.5, 8.2Hz), 7.80(brd, 1H), 8.16(d, 1H, J=8.2Hz). |
| (1)-18 | Z | 0.89(t, 3H, J=6.8Hz), 1.25–1.5(m, 6H), 1.73(m, 2H), 2.40(t, 2H, J=7.6Hz), 3.97(s, 3H), 5.26(s, 2H), 7.00(d, 1H, J=7.0Hz), 7.3–7.55(m, 5H), 7.70(dd, 1H, J=7.0, 8.2Hz), 7.86(brd, 1H), 8.15(d, 1H, J=8.2Hz). |
| (1)-21 | Z | 0.87–0.93(m, 2H), 1.08–1.13(m, 2H), 1.52–1.55(m, 1H), 3.97(s, 3H), 5.27(s, 2H), 7.00(d, J=7.5Hz, 1H), 7.35–7.53(m, 5H), 7.68(d, d, J=7.5Hz, J=8.0Hz, 1H), 8.11(d, J=8.0Hz, 1H). |
| (1)-23 | Z | 1.31–2.05(m, 10H), 2.262.31(m, 1H), 3.97(s, 3H), 5.26(s, 2H), 6.99(d, J=7.5Hz, 1H), 7.35–7.52(m, 5H), 7.72(d, d, J=7.5Hz, J=8.3Hz, 1H), 8.15(d, J=8.3Hz, 1H). |

TABLE 26

| Compound No. | Z/E | $^1$H-NMR (CDCl$_3$) δ |
|---|---|---|
| (2)-7 | Z | 1.29(d, 6H, J=6.8Hz), 2.63(seq, 1H, J=6.8Hz), 3.95(s, 3H), 5.25(s, 2H), 6.92(s, 1H), 7, 3–7.5(m, 3H), 7.52(m, 2H), 8.78(brd, 1H). |
| (2)-11 | Z | 1.33(s, 9H), 3.95(s, 3H), 5.27(s, 2H), 6.92(s, 1H), 7.3–7.5(m, 3H), 7.52(m, 2H), 8.89(brd, 1H). |
| (2)-12 | Z | 0.90(t, 3H, J=7.1Hz), 1.2–1.4(m, 4H), 1.73(m, 2H), 2.44(t, 2H, J=7.5Hz), 3.93(s, 3H), 5.24(s, 2H), 6.91(s, 1H), 7.3–7.55(m, 5H), 9.17(brd, 1H). |
| (2)-18 | Z | 0.87(t, 3H, J=6.8Hz), 1.30(m, 6H), 1.72(m, 4H), 2.44(t, 2H, J=7.5Hz), 3.92(s, 3H), 5.24(s, 2H), 6.91(s, 1H), 7.3–7.55(m, 5H), 9.35(brd, 1H). |
| (2)-19 | Z | 0.87(t, 1H, J=6.8Hz), 1.2–1.4(m, 8H), 1.71(m, 2H), 2.44(t, 2H, J=7.5Hz), 3.92(s, 3H), 5.23(s, 2H), 6.91(s, 1H), 7.3–7.55(m, 5H), 9.48(brd, 1H). |

TABLE 27

| Compound No. | Z/E | ¹H-NMR (CDCl₃) δ |
|---|---|---|
| (3)-2 | Z | 1.26(t, J=7.2Hz, 3H), 3.98(s, 3H), 4.12(q, J=7.2Hz, 2H), 5.26(s, 2H), 6.95(d, J=7.7Hz, 1H), 7.26–7.52(m, 5H), 7.68(d, d, J=7.7Hz, J=8.2Hz, 1H), 7.90(d, J=8.2Hz, 1H). |
| (3)-2 | E | 1.33(t, J=7.2Hz, 3H), 4.00(s, 3H), 5.13(s, 2H), 7.15(d, J=7.3Hz, 1H), 7.26–7.52(m, 5H), 7.80(d, d, J=7.3Hz, J=8.1Hz, 1H), 8.10(d, J=8.1Hz, 1H). |
| (3)-3 | Z | 0.97(t, 3H, J=7.4Hz), 1.70(tq, 2H, J=6.7, 7.4Hz), 3.97(s, 3H), 4.14(t, 2H, J=6.7Hz), 5.26(s, 2H), 6.96(d, 1H, J=7.0Hz), 7.3–7.55(m, 6H), 7.68(dd, 1H, J=7.0, 8.4Hz), 7.90(d, 1H, J=8.4Hz). |
| (3)-4 | Z | 1.30(d, 6H, J=6.2Hz), 3.98(s, 3H), 5.03(seq, 1H, J=6.2Hz), 5.26(s, 2H), 6.95(d, 1H, J=7.0Hz), 7.3–7.55(m, 6H), 7.67(dd, 1H, J=7.0, 8.3Hz), 7.89(d, 1H, J=8.3Hz). |
| (3)-5 | Z | 0.95(t, 3H, J=7.3Hz), 1.40(tq, 2H, J=7.3, 7.3Hz), 1.66(tt, 2H, J=6.6, 7.3Hz), 3.97(s, 3H), 4.18(t, 2H, J=6.6Hz), 5.26(s, 2H), 6.95(d, 1H, J=7.3Hz), 7.25–7.6(m, 6H), 7.68(dd, 1H, J=7.3, 8.3Hz), 7.90(d, 1H, J=8.3Hz). |
| (3)-8 | Z | 1.5(s, 9H), 3.97(s, 3H), 5.25(s, 2H), 6.92(d, J=7.5Hz, 1H), 7.34–7.53(m, 5H), 7.64(d, d, J=7.5Hz, J=8.2Hz, 1H), 7.86(d, J=8.2Hz, 1H). |

TABLE 28

| Compound No. | Z/E | ¹H-NMR (CDCl₃) δ |
|---|---|---|
| (3)-9 | Z | 0.91(t, 3H, J=7.1Hz), 1.35(m, 4H), 1.68(m, 2H), 3.98(s, 3H), 4.18(t, 2H, J=6.7Hz), 5.26(s, 2H), 6.95(d, 1H, J=6.8Hz), 7.3–7.55(m, 6H), 7.68(dd, 1H, J=6.8, 8.3Hz), 7.90(d, 1H, J=8.3Hz). |
| (3)-15 | Z | 0.90(t, 3H, J=7.0Hz), 1.25–1.45(m, 6H), 1.68(m, 2H), 3.98(s, 3H), 4.18(t, 2H, J=6.8Hz), 5.26(s, 2H), 6.95(d, 1H, J=7.7Hz), 7.3–7.55(m, 6H), 7.68(dd, 1H, J=7.7, 8.4Hz), 7.90(d, 1H, J=8.4Hz). |
| (3)-16 | Z | 0.89(t, 3H, J=6.8Hz), 1.2–1.4(m, 8H), 1.68(m, 2H), 3.97(s, 3H), 4.18(t, J=6.8Hz, 2H), 5.26(s, 2H), 6.95(s, 1H), 7.3–7.55(m, 6H), 7.68(dd, 1H, J=7.3.7.9Hz), 7.90(d, J=7.9Hz, 1H). |
| (3)-18 | Z | 3.96(s, 3H), 5.22(s, 2H), 5.24(s, 2H), 6.95(d, 1H, J=7.3Hz), 7.3–7.55(m, 5H), 7.68(dd, 1H, J=7.3, 8.2Hz), 7.91(d, 1H, J=8.2Hz). |
| (3)-21 | Z | 0.92(t, 3H, J=7.5Hz), 1.49(s, 6H), 1.83(q, 2H, J=7.5Hz), 3.97(s, 3H), 5.25(s, 2H), 6.93(d, 1H, J=7.0Hz), 7.2–7.55(m, 6H), 7.65(dd, 1H, J=7.0, 8.2Hz), 7.86(d, 1H, J=8.2Hz). |
| (3)-22 | Z | 1.2–1.6(m, 6H), 1.75(m, 2H), 1.89(m, 2H), 3.97(s, 3H), 4.77(m, 1H), 5.26(s, 2H), 6.95(d, 1H, J=6.8Hz), 7.3–7.55(m, 6H), 7.67(dd, 1H, J=6.8, 8.3Hz), 7.89(d, 1H, J=8.3Hz). |

TABLE 29

| Compound No. | Z/E | ¹H-NMR (CDCl₃) δ |
|---|---|---|
| (4)-3 | Z | 3.36(s, 3H), 3.61(t, J=4.6Hz, 2H), 3.87(s, 3H), 4.37(t, J=4.6Hz, 2H), 5.31(s, 2H), 6.91(s, 1H), 7.31–7.51(m, 5H). |
| (4)-5 | Z | 0.93(t, J=7.3Hz, 3H), 1.32–1.45(m, 2H), 1.63–1.73(m, 2H), 3.87(s, 3H), 4.27(t, J=6.8Hz, 2H), 5.29(s, 2H), 6.89(s, 1H), 7.32–7.61(m, 5H), 10.18(brd, 1H). |
| (4)-9 | Z | 0.89(t, 3H, J=7.0Hz), 1.34(m, 4H), 1.68(m, 2H), 3.87(s, 3H), 4.23(t, 2H, J=6.9Hz), 5.30(s, 2H), 6.89(s, 1H), 7.3–7.55(m, 5H), 10.21(brd, 1H). |
| (4)-15 | Z | 0.87(t, 3H, J=6.7Hz), 1.2–1.45(m, 6H), 1.69(m, 2H), 3.86(s, 3H), 4.22(t, 2H, J=6.9Hz), 5.31(s, 2H), 6.89(s, 1H), 7.25–7.55(m, 5H), 10.50(brd, 1H). |

TABLE 29-continued

| Compound No. | Z/E | $^1$H-NMR (CDCl$_3$) δ |
| --- | --- | --- |
| (4)-16 | Z | 0.87(t, J=6.9Hz, 3H), 1.24–1.31(m, 7H), 1.64–1.72(m, 3H), 3.88(s, 3H), 4.23(t, J=6.8Hz, 2H), 5.29(s, 2H), 6.89(s, 1H), 7.31–7.52(m, 5H), 9.94(brd, 1H) |
| (4)-18 | Z | 3.79(s, 3H), 5.10(s, 2H), 5.22(s, 2H), 6.85(s, 1H), 7.2–7.55(m, 10H), 10.89(brd, 1H). |
| (5)-1 | Z | 3.52(s, 3H), 3.99(s, 3H), 4.04(s, 2H), 5.29(s, 2H), 7.04(d, J=7.1Hz, 1H), 7.34–7.53(m, 4H), 7.72(dd, J=7.9Hz, J=7.9Hz, 1H), 8.18(d, J=8.3Hz), 8.81(brd, 1H). |
| (5)-2 | Z | 1.32(t, J=7.0Hz), 3.67(q, J=7.0Hz, 2H), 4.00(s, 3H), 4.07(s, 2H), 5.30(s, 2H), 7.04(d, J=7.5Hz, 1H), 7.34–7.55(m, 4H), 7.72(dd, J=7.9, J=7.9Hz, 1H), 8.18(d, J=8.3Hz), 8.85(brd, 1H). |

TABLE 30

| Compound No. | Z/E | $^1$H-NMR (CDCl$_3$) δ |
| --- | --- | --- |
| (5)-10 | Z | 1.08(t, J=7.3Hz, 3H), 2.24–2.31(m, 2H), 3.96(s, 3H), 5.26(s, 2H), 5.95(d, J=15.2Hz, 1H), 7.01(d, J=7.3Hz, 1H), 7.10(t, J=6.4Hz, 1H), 7.33–7.51(m, 5H), 7.69(d, d, J=7.3Hz, J=8.2Hz, 1H), 8.22(d, J=8.2Hz, 1H). |
| (5)-12 | Z | 3.76(s, 2H), 3.89(s, 3H), 5.20(s, 2H), 6.99(d, 1H, J=7.0Hz), 7.25–7.55(m, 10H), 7.68(dd, 1H, J=7.0, J=8.3Hz), 7.82(brd, 1H), 8.15(d, 1H, J=8.3Hz). |
| (6)-1 | Z | 3.51(s, 3H), 3.95(s, 3H), 4.12(s, 2H), 5.27(s, 2H), 6.95(s, 1H), 7.35–7.55(m, 5H), 9.65(brd, 1H). |
| (6)-2 | Z | 1.29(t, J=7.1Hz, 3H), 3.66(q, J=7.0Hz, 2H), 3.95(s, 3H), 4.17(s, 2H), 5.28(s, 2H), 6.93(s, 1H), 7.35–7.54(m, 5H), 9.65(brd, 1H). |
| (6)-3 | Z | 1.27(t, J=6.7Hz, 3H), 2.73(t, J=5.6Hz, 2H), 3.62(q, J=7.0Hz), 3.77(t, J=5.6Hz, 2H), 3.96(s, 2H), 6.91(s, 1H), 7.34–7.61(m, 5H). |
| (6)-6 | Z | 2.15(s, 3H), 2.76(t, J=6.7Hz, 2H), 2.89(t, J=7.1Hz, 2H), 3.93(s, 3H), 5.24(s, 2H), 6.93(s, 1H), 7.33–7.53(m, 5H), 9.70(brd, 1H). |
| (6)-7 | Z | 2.06(s, 3H), 3.91(s, 3H), 5.24(s, 2H), 5.58(s, 1H), 5.93(s, 1H), 6.94(s, 1H), 7.33–7.52(m, 5H). |

TABLE 31

| Compound No. | Z/E | $^1$H-NMR (CDCl$_3$) δ |
| --- | --- | --- |
| (7)-1 | Z | 1.01(t, 3H, J=7.3Hz), 1.76(qt, 2H, J=7.3, 7.4Hz), 2.37(t, 2H, J=7.4Hz), 3.97(s, 3H), 5.26(s, 2H), 6.99(d, 1H, J=7.5Hz), 7.35(m, 2H), 7.47(m, 2H), 7.70(dd, 1H, J=7.5, 8.4Hz), 7.86(brd, 1H), 8.17(d, 1H, J=8.4Hz). |
| (7)-2 | Z | 1.27(d, 2H, J=7.0Hz), 2.56(seq, 1H, J=7.0Hz), 3.98(s, 3H), 5.27(s, 2H), 6.98(d, 1H, J=7.0Hz), 7.35(m, 2H), 7.47(m, 2H), 7.70(dd, 1H, J=7.0, 8.1Hz), 7.8(brd, 1H), 8.17(d, 1H, J=8.1Hz). |
| (7)-3 | Z | 0.90(m, 2H), 1.11(m, 2H), 1.55(m, 1H), 3.98(s, 3H), 5.27(s, 2H), 6.98(d, 1H, J=6.6Hz), 7.36(m, 2H), 7.47(m, 2H), 7.69(dd, 1H, J=6.6, 8.1Hz), 8.05(brd, 1H), 8.12(d, 1H, J=8.1Hz). |
| (7)-4 | Z | 1.26(t, 3H, J=7.5Hz), 2.44(q, 2H, J=7.5Hz), 3.98(s, 3H), 5.27(s, 2H), 7.00(d, 1H, J=7.3Hz), 7.1–7.25(m, 2H), 7.3–7.4(m, 2H), 7.71(dd, 1H, J=7.3, 8.4Hz), 7.85(brd, 1H), 8.16(d, 1H, J=8.4Hz). |
| (7)-5 | Z | 1.27(d, 6H, J=7.0Hz), 2.56(seq, 1H, J=7.0Hz), 3.98(s, 3H), 5.28(s, 2H), 7.00(d, 1H, J=7.5Hz), 7.1–7.25(m, 2H), 7.3–7.4(m, 2H), 7.70(dd, 1H, J=7.5, 8.1Hz), 7.87(brd, 1H), 8.18(d, 1H, J=8.1Hz). |
| (7)-6 | Z | 1.92(m, 2H), 1.11(m, 2H), 1.56(m, 1H), 3.98(s, 3H), 5.28(s, 2H), 6.99(d, 1H, J=6.6Hz), 7.1–7.25(m, 2H), 7.25–7.45(m, 2H), 7.69(dd, 1H, J=6.6, 8.1Hz), 8.13(d, 1H, J=8.1Hz), 8.1(brd, 1H). |

TABLE 32

| Compound No. | Z/E | ¹H-NMR (CDCl₃) δ |
|---|---|---|
| (7)-8 | Z | 1.26(d, 6H, J=7.0Hz), 2.55(seq, 1H, J=7.0Hz), 3.98(s, 3H), 5.26(s, 2H), 7.00(d, 1H, J=7.7Hz), 7.07(m, 2H), 7.52(m, 2H), 7.70(dd, 1H, J=7.7, 8.4Hz), 7.91(brd, 1H), 8.18(d, 1H, J=8.4Hz). |
| (7)-9 | Z | 1.27(d, 6H, J=7.0Hz), 2.56(seq, 1H, J=7.0Hz), 3.82(s, 3H), 3.97(s, 3H), 5.23(s, 2H), 6.90(m, 2H), 6.99(d, 1H, J=6.8Hz), 7.44(m, 2H), 7.69(dd, 1H, J=6.8, J=7.9Hz), 7.86(brd, 1H), 8.15(d, 1H, J=7.9Hz). |
| (7)-11 | Z | 1.90(m, 2H), 1.18(m, 2H), 1.56(m, 1H), 3.82(s, 3H), 3.97(s, 3H), 5.23(s, 2H), 6.88(m, 2H), 6.98(d, 1H, J=6.8Hz), 7.44(m, 2H), 7.67(dd, 1H, J=6.8, 7.9Hz), 8.10(d, 1H, J=7.9Hz), 8.14(brd, 1H). |
| (7)-12 | Z | 1.91(t, 3H, J=7.0Hz), 1.35(m, 4H), 1.73(m, 2H), 2.37(s, 3H), 2.39(t, 2H, J=7.5Hz), 3.96(s, 3H), 5.24(s, 2H), 6.99(d, 1H, J=7.3Hz), 7.17(m, 2H), 7.38(m, 2H), 7.69(dd, 1H, J=7.3, 8.4Hz), 7.89(brd, 1H), 8.14(d, 1H, J=8.4Hz). |
| (7)-13 | Z | 1.11(s, 9H), 2.26(s, 2H), 2.37(s, 3H), 3.96(s, 3H), 5.24(s, 2H), 7.00(d, 1H, J=7.0Hz), 7.17(m, 2H), 7.38(m, 2H), 7.68(dd, 1H, J=7.0, 8.2Hz), 7.85(brd, 1H), 8.16(d, 1H, J=8.2H). |

TABLE 33

| Compound No. | Z/E | ¹H-NMR (CDCl₃) δ |
|---|---|---|
| (7)-14 | Z | 1.28(d, 6H, J=7.0Hz), 2.64(seq, 1H, J=7.0Hz), 4.04(s, 3H) 5.40(s, 2H), 7.3–7.5(m, 3H), 7.55(m, 2H), 7.78(d, 1H, J=86Hz), 8.07(d, 1H, J=8.6Hz), 8.38(brd, 1H). |
| (7)-17 | Z | 1.27(d, 6H, J=6.8Hz), 1.45(t, 3H, J=7.3Hz), 2.56(seq, 1H, J=6.8Hz), 4.28(q, 2H, J=7.3Hz), 5.25(s, 2H), 7.00(d, 1H, J=6.8Hz), 7.3–7.5(m, 5H), 7.69(dd, 1H, J=6.8, 8.0Hz), 7.88(brd, 1H), 8.16(d, 1H, J=8.0Hz). |
| (7)-18 | Z | 4.02(s, 3H), 5.41(s, 2H), 7.07(m, 2H), 7.25(m, 2H), 7.54(m, 2H), 7.70(ddd, 1H, J=2.0, 7.7Hz, 7.7Hz), 8.59(d, 1H, J=4.8Hz). |
| (7)-19 | Z | 4.02(s, 3H), 5.42(s, 2H), 7.14(dddd, 1H, J=1.0Hz, 2.6Hz, 7.7Hz, 7.7Hz), 7.18–7.4(m, 5H), 7.70(ddd, 1H, J=1.8Hz, 7.7Hz, 7.7Hz), 8.59(m, 1H). |
| (7)-20 | Z | 4.01(s, 3H), 5.41(s, 2H), 7.24(m, 2H), 7.35(m, 2H), 7.48(m, 2H), 7.70(ddd, 1H, J=1.8Hz, 7.7Hz, 7.7Hz), 8.59(ddd, 1H, J=1.5Hz, 1.8Hz, 4.4Hz). |
| (8)-2 | Z | 1.27(d, 6H, J=7.0Hz), 2.64(seq, 1H, J=7.0Hz), 3.92(s, 3H), 5.24(s, 2H), 6.93(s, 1H), 7.34(m, 2H), 7.47(m, 2H), 9.20(brd, 1H). |

TABLE 34

| Compound No. | Z/E | ¹H-NMR (CDCl₃) δ |
|---|---|---|
| (8)-7 | Z | 1.33(s, 9H), 3.96(s, 3H), 5.27(s, 2H), 6.93(s, 1H), 7.1–7.43(m, 4H), 8.95(brd, 1H). |
| (8)-9 | Z | 1.29(d, 6H, J=7.0Hz), 2.63(seq, 1H, J=7.0Hz), 3.83(s, 3H), 3.94(s, 3H), 5.22(s, 2H), 6.88(m, 3H), 7.46(m, 2H), 8.87(brd, 1H). |
| (8)-10 | Z | 1.33(s, 9H), 3.83(s, 3H), 3.94(s, 3H), 5.22(s, 2H), 6.89(m, 3H), 7.46(m, 2H), 8.99(brd, 1H). |
| (8)-12 | Z | 0.91(t, J=7.1Hz, 3H), 1.31–1.38(m, 4H), 1.70–1.77(m, 2H), 5.23(s, 2H), 6.92(s, 1H), 7.34–7.53(m, 5H), 9.10(brd, 1H) |
| (8)-15 | Z | 1.26(d, 6H, J=7.0Hz), 1.42(t, 3H, J=7.3Hz), 2.65(seq, 1H, J=7.0Hz), 4.26(q, 2H, J=7.3Hz), 5.19(s, 2H), 7.3–7.5(m, 5H), 9.12(brd, 1H). |
| (9)-1 | Z | 1.52(s, 9H), 3.98(s, 3H), 5.26(s, 2H), 6.92(d, 1H, J=7.7Hz), 7.17.4(m, 5H), 7.66(dd, 1H, J=7.7, 8.4Hz), 7.88(d, 1H, J=8.4Hz). |
| (9)-2 | Z | 1.31(d, 6H, J=6.4Hz), 3.99(s, 3H), 5.03(seq, 1H, J=6.4Hz), 5.25(s, 2H), 6.93(d, 1H, J=7.2Hz), 7.07(m, 2H), 7.28(brd, 1H), 7.53(m, 2H), 7.68(d, 1H, J=7.2, 8.4Hz), 7.90(d, 1H, J=8.4Hz). 1.52(s, 9H), 3.98(s, 3H), 5.24(s, 2H), 6.91(d, 1H, J=7.3Hz), 7.07(m, 2H), 7.19(brd, 1H), 7.53(m, 2H), 7.65(dd, 1H, J=7.3, 8.4Hz), 7.87(d, 1H, J=8.4Hz). |

TABLE 35

| Compound No. | Z/E | $^1$H-NMR(CDCl$_3$)δ |
|---|---|---|
| (9)-3 | Z | |
| (9)-4 | Z | 1.52(s, 9H), 2.36(s, 3H), 3.95(s, 3H), 5.23(s, 2H), 6.92(d, 1H, J=7.2Hz), 7.17(m, 2H), 7.31 (brd, 1H), 7.39(m, 2H), 7.64(dd, 1H, J=7.2, 8.4Hz), 7.86(d, 1H, J=8.4Hz). |
| (9)-5 | Z | 0.92(t, 3H, J=7.0Hz), 1.36(m, 4H), 1.68(m, 2H), 2.36(s, 3H), 3.96(s, 3H), 4.17(t, 2H, J=6.7Hz), 5.24(s, 2H), 6.95(d, 1H, J=7.5Hz), 7.17(m, 2H), 7.38(m, 2H), 7.46(brd, 1H), 7.67(dd, 1H, J=7.5, 8.1Hz), 7.89(d, 1H, J=8.1Hz). |
| (9)-6 | Z | 0.98(t, 3H, J=7.4Hz), 1.71(tq, 2H, J=6.7, 7.4Hz), 3.99(s, 3H), 4.15(q, 2H, J=6.7Hz), 6.95(d, 1H, J=7.0H), 7.1–7.25(m, 2H), 7.3–7.45(m, 3H), 7.69(dd, 1H, J=7.0, 8.3Hz), 7.91(d, 1H, J=8.3Hz). |
| (9)-7 | Z | 0.91(t, 3H, J=7.1Hz), 1.36(m, 4H), 1.73(m, 2H), 2.33(s, 3H), 2.39(q, 2H, J=7.5Hz), 3.96(s, 3H), 5.26(s, 2H), 7.00(d, 1H, J=7.5Hz), 7.27(m, 4H), 7.69(dd, 1H, J=7.5, 8.3Hz), 7.89(brd, 1H), 8.15(d, 1H, J=8.3Hz). |
| (9)-8 | Z | 1.52(s, 9H), 2.33(s, 3H), 3.96(s, 3H), 5.24(s, 2H), 6.92(d, 1H, J=6.8Hz), 7.2–7.35(m, 5H), 7.65(dd, 1H, J=6.8Hz), 7.86(d, 1H, J=8.3Hz). |
| (9)-9 | Z | 0.93(t, 3H, J=7.5Hz), 1.49(s, 6H), 1.83(q, 2H, J=7.5Hz), 2.36(s, 3H), 3.96(s, H), 5.23(s, 2H), 6.92(d, 1H, J=7.0Hz), 7.19(m, 3H), 7.39(m, 2H), 7.64(dd, 1H, J=7.0, 8.3Hz), 7.85(d, 1H, J=8.3Hz). |

TABLE 36

| Compound No. | Z/E | $^1$H-NMR (CDCl$_3$) δ |
|---|---|---|
| (11)-4 | Z | 2.21(s, 3H), 2.49(s, 3H), 5.24(s, 2H), 7.00(d, J=7.5Hz, 1H), 7.34–7.53(m, 5H), 7.71(dd, J=7.9Hz, 1H), 7.90(brd, 1H), 8.13(d, J=8.3Hz, 1H). |
| (11)-5 | Z | 1.26(t, J=7.5Hz, 3H), 2.44(q, J=7.5Hz, 2H), 2.49(s, 3H), 5.24(s, 2H), 6.99(d, J=7.5Hz, 1H), 7.34–7.50(m, 5H), 7.71(dd, J=7.8Hz, 1H), 7.79(brd, 1H), 8.16(d, J=8.2Hz, 1H). |
| (11)-6 | Z | 1.02(t, J=7.3Hz, 7.5Hz, 3H), 1.78(m, 2H), 2.38(t, J=7.3Hz, 7.5Hz, 2H), 2.49(s, 3H), 5.24(s, 2H), 6.99(d, J=6.8Hz, 1H), 7.34–7.52(m, 5H), 7.70(dd, J=7.7Hz, 8.0Hz, 1H), 7.77(brd, 1H), 8.16(d, J=8.4Hz, 1H). |
| (11)-7 | Z | 1.27(d, J=7.0Hz, 6H), 2.49(s, 3H), 2.51(qq, J=6.8Hz, 1H), 5.24(s, 2H), 6.99(d, J=7.5Hz, 1H), 7.35–7.55(m, 5H), 7.70(dd, J=7.7Hz, 8.3Hz, 1H), 7.80(brd, 1H), 8.17(d, J=8.4Hz, 1H). |
| (11)-8 | Z | 0.95(t, J=7.3Hz, 3H), 1.42(m, 2H), 1.2(m, 2H), 2.40(t, J=7.3Hz, 2H), 2.49(s, 3H), 5.24(s, 2H), 6.99(d, J=7.5Hz, 2H), 7.34–7.53(m, 5H), 7.70(dd, J=7.9Hz, 1H), 7.80(brd, 1H), 8.16(d, J=8.3Hz, 1H). |
| (11)-11 | Z | 1.33(s, 9H), 2.50(s, 3H), 5.25(s, 2H), 6.99(d, J=7.5Hz, 1H), 7.35–7.53(m, 5H), 7.70(dd, J=7.7Hz, 8.0Hz, 1H), 7.97(brd, 1H), 8.19(d, J=8.3Hz, 1H). |

TABLE 37

| Compound No. | Z/E | $^1$H-NMR (CDCl$_3$) δ |
|---|---|---|
| (11)-18 | Z | 0.89(t, J=6.6Hz, 7.1Hz, 3H), 1.26–1.42(m, 6H), 1.68–1.75(m, 2H), 2.40(t, J=7.4Hz, 7.7Hz, 2H), 2.49(s, 3H), 5.24(s, 2H), 6.99(d, J=7.5Hz, 1H), 7.34–7.52(m, 5H), 7.70(dd, J=7.9Hz, 8.1Hz, 1H), 7.86(brd, 1H), 8.16(d, J=8.2Hz, 1H). |
| (11)-19 | Z | 0.88(t, J=7.00, 3H), 1.23–1.36(m, 8H), 1.68–1.78(m, 2H), 2.42(t, J=7.5Hz, 2H), 2.49(s, 3H), 5.24(s, 2H), 6.98(d, J=7.5Hz, 1H), 7.37–7.52(m, 5H), 7.70(dd, J=7.5Hz, 8.2Hz, 1H), 7.79(brd, 1H), 8.15(d, J=8.2Hz, 1H). |
| (11)-21 | Z | 0.87–0.93(m, 2H), 1.09–1.14(m, 2H), 1.51–1.62(m, 1H), 2.49(s, 3H), 5.25(s, 2H), 6.98(d, J=7.5Hz, 1H), 7.35–7.52(m, 5H), 7.69(dd, J=7.8Hz, 7.9Hz, 1H), 8.03(brd, 1H), 8.12(d, J=8.6Hz, 1H). |

TABLE 37-continued

| Compound No. | Z/E | $^1$H-NMR (CDCl$_3$) δ |
|---|---|---|
| (11)-22 | Z | 1.62–2.16(m, 8H), 2.49(s, 3H), 2.73(tt, J=7.7Hz, 8.0Hz, 1H), 5.24(s, 2H), 6.99(d, J=6.7Hz, 1H), 7.34–7.53(m, 5H), 7.70.(dd, J=7.7Hz, 8.0Hz, 1H), 7.81(brd, 1H), 8.17(d, J=8.4Hz, 1H). |
| (11)-23 | Z | 1.22–1.99(m, 10H), 2.27(tt, J=3.5Hz, 11.6Hz, 1H), 2.49(s, 3H), 5.24(s, 2H), 6.98(d, J=7.4Hz, 1H), 7.34–7.53(m, 5H), 7.69(dd, J=7.9Hz, 1H), 7.83(brd, 1H), 8.17(d, J=7.9Hz, 1H). |
| (12)-3 | Z | 2.43(s, 3H), 5.25(s, 2H), 7.02(s, 1H)7.32–7.52(m, 5H), 8.54(s, 1H), 11.50(brd, 1H). |

TABLE 38

| Compound No. | Z/E | $^1$H-NMR (CDCl$_3$) δ |
|---|---|---|
| (12)-7 | Z | 1.25–1.28(m, 6H), 2.46(s, 3H), 2.58–2.73(m, 1H), 5.23(s, 2H), 6.93(s, 1H), 7.20–7.54(m, 5H), 9.43(brd, 1H). |
| (12)-8 | Z | 0.95(t, 3H, J=7.33Hz), 1.35–1.47(m, 2H), 1.68–1.78(m, 2H), 2.43–2.48(m, 5H), 5.23(s, 1H), 6.91(s, 1H), 7.35–7.52(m, 5H), 8.74(brd, 1H). |
| (12)-9 | Z | 1.62(d, 6H, J=6.43Hz), 2.20–2.30(m, 1H), 2.32(d, 2H, J=6.58Hz), 2.47(s, 3H), 5.23(s, 2H), 6.91(s, 1H), 7.38–7.50(m, 5H), 8.62(brd, 1H). |
| (12)-16 | Z | 1.10(s, 9H), 2.31(s, 2H), 2.47(s, 3H), 5.23((s, 2H), 6.91(s, 1H), 7.36–7.61(m, 5H), 8.60(brd, 1H). |
| (12)-18 | Z | 0.84–0.88(m, 3H), 1.23–1.40(m, 6H), 1.67–1.77(m, 2H), 2.45–2.55(m, 5H), 5.23(s, 2H), 6.93(s, 1H), 7.33–7.73(m, 5H), 9.80(brd, 1H). |
| (12)-19 | Z | 0.85–0.90(m, 3H), 1.23–1.39(m, 8H), 1.66–1.78(m, 2H), 2.24–2.48(m, 5H), 5.23(s, 2H), 6.91(s, 1H), 7.34–7.52(m, 5H), 8.95(brd, 1H). |
| (13)-1 | Z | 2.50(s, 3H), 3.80(s, 3H), , 5.24(s, 2H), 6.94(d, J=7.0Hz, 1H), 7.34–7.43(m, 5H), 7.72(dd, J=7.0Hz, J=8.6Hz, 1H), 7.93(d, J=8.6Hz, 1H). |
| (13)-2 | Z | 1.32(t, J=7.0Hz, 3H), 2.50(s, 3H), 4.31(q, J=7.0Hz, 2H), 5.24(s, 2H), 6.96(d, J=7.1Hz, 1H), 7.33–7.45(m, 5H), 7.74(dd, J=7.1Hz, J=8.6Hz, 1H), 7.96(d, J=8.6Hz, 1H). |

TABLE 39

| Compound No. | Z/E | $^1$H-NMR (CDCl$_3$) δ |
|---|---|---|
| (13)-3 | Z | 0.93(t, J=6.8Hz, 3H), 1.72(tq. J=6.7Hz, J=6.8Hz, 2H), 2.49(s, 3H), 4.14(t, J=6.7Hz, 2H), 5.25(s, 2H), 6.94(d, J=6.8Hz, 1H), 7.34–7.53(m, 5H), 7.69(dd, J=6.8Hz, J=8.4Hz, 1H), 7.90(d, J=8.4Hz, 1H). |
| (13)-5 | Z | 0.95(t, J=7.3Hz, 3H), 1.43–1.72(m, 4H), 2.49(s, 3H), 4.19(t, J=6.6Hz, 2H), 5.23(s, 2H), 6.93(d, 7.5Hz, 1H), 7.35–7.52(m, 5H), 7.68(dd, J=7.5Hz, J=8.2Hz, 1H), 7.90(d, J=8.2Hz, 1H). |
| (13)-6 | Z | 0.96(d, J=6.8Hz, 6H), 1.98(sept, J=6.8Hz, 1H), 2.49(s, 3H), 3.95(d, J=6.6Hz, 2H), 5.24(s, 1H), 6.94(d, J=8.0Hz, 1H), 7.32–7.52(m, 5H), 7.68(dd, J=8.0Hz, J=8.2Hz, 1H), 7.90(d, J=8.2Hz, 1H). |
| (13)-6 | E | 0.96(d, J=6.8Hz, 6H), 1.98(sept, J=6.8Hz, 1H), 2.49(s, 3H), 3.95(d, J=6.6Hz, 2H), 5.22(s, 1H), 6.92(d, J=8.0Hz, 1H), 7.32–7.52(m, 5H), 7.66(dd, J=8.0Hz, J=8.2Hz, 1H), 7.78(d, J=8.2Hz, 1H). |
| (13)-15 | Z | 0.90(t, J=6.6Hz, 3H), 1.33–1.43(m, 6H), 1.63–1.72(m, 2H), 2.50(s, 3H), 4.18(t, J=6.6Hz, 2H), 5.24(s, 2H), 6.93(d, J=7.0Hz, J=8.2Hz, 1H), 7.90(d, J=8.2Hz, 1H). |
| (13)-21 | Z | 1.61–1.95(m, 8H), 2.49(s, 3H), 5.20(m, 1H), 5.23(s, 2H), 6.92(d, J=7.0Hz, 1H), 7.357.52(m, 5H), 7.68(dd, J=7.0Hz, J=8.3Hz, 1H), 7.89(d, J=8.3Hz, 1H). |

TABLE 40

| Compound No. | Z/E | $^1$H-NMR (CDCl$_3$) δ |
|---|---|---|
| (13)-22 | Z | 1.23–1.94(m, 10H), 2.50(, s, 3H), 4.73–4.81(m, 1H), 5.24(s, 2H), 6.93(d, J=7.0Hz, 1H), 7.35–7.52(m, 5H), 7.65(dd, J=7.7Hz, 8.1Hz, 1H), 7.90(d, J=8.3Hz, 1H). |
| (14)-3 | Z | 0.94(t, 3H, J=7.5Hz), 1.73(m, 2H), 2.34(s, 3H), 4.15(m, 2H), 5.33(s, 2H), 6.94(s, 1H), 7.29–7.49(m, 5H), 11.28(brs, 1H). |
| (14)-5 | Z | 0.94(t, 3H, J=7.33Hz), 1.33–1.46(m, 2H), 1.591.73(m, 2H), 2.42(s, 3H), 4.25(t, 2H, J=6.76Hz), 5.25(s, 2H), 6.88(s, 1H), 7.33–7.50(m, 5H), 9.40(brd, 1H). |
| (14)-9 | Z | 0.90(t, J=6.8Hz3H), 1.32–1.38(m, 4H), 1.65–1.72(m, 2H), 2.38(s, 3H), 4.26(q, J=7.0Hz, 2H), 5.39(s, 2H), 6.93(s, 1H), 7.31–7.61(m, 5H). |
| (14)-15 | Z | 0.88(t, 3H, J=6.61Hz), 1.24–1.32(m, 6H), 1.65–1.72(m, 2H), 2.44(s, 3H), 4.24(t, 2H, J=6.79Hz), 5.25(s, 2H), 6.88(s, 1H), 7.34–7.50(m, 5H), 9.05(brd, 1H). |
| (16)-3 | Z | 2.46(s, 3H), 5.25(s, 2H), 6.99(s, 1H), 7.36–7.65(m, 8H), 7.91–7.94(m, 2H), 9.63(brd, 1H). |
| (17)-21 | Z | 0.91(t, J=7.1Hz, 3H), 1.32(t, J=7.6Hz, 3H), 1.34(m, 4H), 1.74(m, 2H), 2.39(t, J=7.5Hz, 2H), 2.79(q, J=7.6Hz, 2H), 5.23(s, 2H), 6.99(d, J=7.5Hz, 1H), 7.2–7.6(m, 5H), 7.70(dd, J=7.5Hz, J=8.4Hz, 1H), 7.81(brd, 1H), 8.16(d, J=8.4Hz, 1H). |

TABLE 41

| Compound No. | Z/E | $^1$H-NMR (CDCl$_3$) δ |
|---|---|---|
| (18)-19 | Z | 0.89(t, J=7.0Hz, 3H), 1.27(t, J=7.7Hz, 3H), 1.2–1.4(m, 4H), 1.73(m, 2H), 2.46(t, J=7.3Hz, 2H), 2.76(q, J=7.7Hz, 2H), 5.22(s, 2H), 6.91(s, 1H), 7.2–7.55(m, 5H), 9.47(brd, 1H). |
| (19)-11 | Z | 0.96(t, 3H, J=7.33Hz), 1.361.48(m, 2H), 1.63–1.72(m, 2H), 2.50(s, 3H), 4.19(t, 2H, J=6.61Hz), 5.23(s, 2H), 6.93(d, 1H, J=7.33Hz), 7.02–7.05(m, 1H), 7.16–7.26(m, 3H), 7.33–7.41(m, 1H), 7.69(t, 1H, J=7.69Hz), 7.92(d, 1H, J=8.44Hz). |
| (19)-12 | Z | 0.95(t, 3H, J=7.33Hz), 1.35–1.48(m, 2H), 1.64–1.72(m, 2H), 2.50(s, 3H), 4.19(t, 2H, J=6.79Hz), 5.23(s, 2H), 6.92(d, 1H, J=6.79Hz), 7.05–7.13(m, 2H), 7.32(brd, 1H), 7.35–7.41(m, 2H), 7.68(t, 1H, J=6.34Hz), 7.91(d, 1H, J=8.26Hz). |
| (19)-13 | Z | 0.96(t, 3H, J=7.33Hz), 1.36–1.48(m, 2H), 1.62–1.72(m, 2H), 2.50(s, 3H), 4.19(t, 2H, J=6.58Hz), 5.25(s, 2H), 6.92(d, 1H, J=7.51Hz), 7.15–7.18(m, 1H), 7.26–7.36(m, 2H), 7.44–7.49(m, 1H), 7.69(t, 1H, J=8.05Hz), 7.92(d, 1H, J=8.23Hz). |
| (19)-14 | Z | 0.96(t, 3H, J=7.33Hz), 1.36–1.48(m, 2H), 1.62–1.72(m, 2H), 2.49(s, 3H), 4.19(t, 2H, J=6.61Hz), 5.23(s, 2H), 6.92(d, 1H, J=7.51Hz), 7.30–7.40(m, 4H), 7.68(t, 1H, J=7.51Hz), 7.91(d, 1H, J=8.26Hz). |

TABLE 42

| Compound No. | Z/E | $^1$H-NMR (CDCl$_3$) δ |
|---|---|---|
| (19)-16 | Z | 0.95(t, 3H, J=7.15Hz), 1.35–1.48(m, 2H), 1.62–1.71(m, 2H), 2.38(s, 3H), 2.48(s, 3H), 4.19(t, 2H, J=6.58Hz), 5.22(s, 2H), 6.93(d, 1H, J=7.33Hz), 7.20–7.30(m, 5H), 7.68(t, 1H, J=7.90Hz), 7.89(d, 1H, J=8.41Hz). |
| (19)-23 | Z | 0.96(t, 3H, J=7.48Hz), 1.36–1.48(m, 2H), 1.62–1.72(m, 2H), 2.49(s, 3H), 3.83(s, 3H), 4.19(t, 2H, J=6.79Hz), 5.20(s, 2H), 6.88–6.94(m, 3H), 7.26–7.31(m, 3H), 7.68(t, 1H, J=7.87Hz), 7.92(d, 1H, J=8.23Hz). |
| (19)-25 | Z | 0.96(t, 3H, J=7.33Hz), 1.36–1.48(m, 2H), 1.63–1.72(m, 2H), 2.51(s, 3H), 4.19(t, 2H, J=6.61Hz), 5.28(s, 2H), 6.92(d, 1H, J=7.15Hz), 7.49–7.53(m, 2H), 7.67–7.72(m, 3H), 7.93(d, 1H, J=8.26Hz). |

TABLE 42-continued

| Compound No. | Z/E | $^1$H-NMR (CDCl$_3$) δ |
|---|---|---|
| (19)-28 | Z | 0.90–0.94(m, 3H), 1.34–1.40(m, 4H), 1.65–1.69(m, 2H), 2.52(s, 3H), 3.07(s, 3H), 4.18(t, 2H, J=6.79Hz), 5.29(s, 2H), 6.93(d, 1H, J=7.51Hz), 7.58–7.62(m, 2H), 7.70(t, 1H, J=7.90Hz), 7.92–8.00(m, 3H). |
| (19)-29 | Z | 0.96(t, 3H, J=7.33Hz), 1.36–1.48(m, 2H), 1.63–1.72(m, 2H), 2.52(s, 3H), 4.20(t, 2H, J=6.61Hz), 5.30(s, 2H), 6.93(d, 1H, J=6.97Hz), 7.56–7.61(m, 2H), 7.70(t, 1H, J=7.69Hz), 7.94(d, 1H, J=8.23Hz), 8.24–8.27(m, 2H). |

TABLE 43

| Compound No. | Z/E | $^1$H-NMR (CDCl$_3$) δ |
|---|---|---|
| (19)-31 | Z | 0.96(t, 3H, J=7.33Hz), 1.34–1.48(m, 2H), 1.63–1.72(m, 2H), 2.51(s, 3H), 4.19(t, 2H, J=6.61Hz), 5.27(s, 2H), 6.93(d, 1H, J=7.33Hz), 7.28(brd, 1H), 7.51(d, 1H, J=8.26), 7.65–7.72(m, 3H), 7.93(d, 1H, J=8.26Hz). |
| (19)-33 | Z | 0.95(t, J=7.3Hz, 3H), 1.32(t, J=7.6Hz, 3H), 1.41(m, 2H), 2.80(q, J=7.6Hz, 2H), 4.19(t, J=6.6Hz, 2H), 5.24(s, 2H), 6.93(d, J=7.0Hz, 1H), 7.2–7.6(m, 6H), 7.68(dd, J=7.0Hz, 8.3Hz, 1H), 7.90(d, J=8.3Hz, 1H). |
| (19)-34 | Z | 0.96(t, 3H, J=7.33Hz), 1.23(t, 3H, J=7.51), 1.35–1.48(m, 2H), 1.67–1.72(m, 2H), 2.49(s, 3H), 2.68(q, 2H, J=7.51), 4.19(t, 2H, J=6.58Hz), 5.21(s, 2H), 6.92(d, 1H, J=7.33Hz), 7.20–7.29(m, 5H), 7.67(t, 1H, J=7.51Hz), 7.89(d, 1H, J=8.26Hz). |
| (19)-36 | Z | 0.96(t, 3H, J=7.33Hz), 1.36–1.48(m, 2H), 1.62–1.72(m, 2H), 2.52(s, 3H), 4.19(t, 2H, J=6.61Hz), 5.25(s, 2H), 6.95(d, 1H, J=7.54Hz), 7.37–7.48(m, 6H), 7.57–7.63(m, 4H), 7.69(t, 1H, J=8.05Hz), 7.91(d, 1H, J=8.26Hz). |
| (19)-37 | Z | 0.94(t, 3H, J=7.33Hz), 1.36–1.46(m, 2H), 1.61–1.71(m, 2H), 2.64(s, 3H), 4.19(t, 2H, J=6.79Hz), 5.29(s, 2H), 6.98(d, 1H, J=7.33Hz).7.34–7.48(m, 3H), 7.59(brd, 1H), 7.64–7.71(m, 2H), 7.95(d, 1H, J=8.08Hz). |

TABLE 44

| Compound No. | Z/E | $^1$H-NMR (CDCl$_3$) δ |
|---|---|---|
| (19)-38 | Z | 0.94(t, 3H, J=7.33Hz), 1.34–1.46(m, 2H), 1.61–1.68(m, 2H), 2.59(s, 3H), 3.50(s, 3H), 4.18(t, 2H, J=6.79Hz), 5.25(s, 2H), 6.84(d, 1H, J=8.05Hz), 6.90–7.11(m, 2H), 7.38–7.48(m, 1H), 7.62–7.73(m, 3H), 7.93(d, 1H, J=8.27Hz). |
| (20)-6 | Z | 0.87(t, J=7.0Hz, 3H), 1.23(t, J=7.7Hz, 3H), 1.2–1.4(m, 6H), 1.69(m, 2H), 2.71(q, J=7.7Hz, 2H), 4.24(t, J=7.0Hz, 2H), 5.30(s, 2H), 6.87(s, 1H), 7.2–7.5(m, 5H), 10.53(brd, 1H). |
| (21)-5 | Z | 0.94(t, J=7.3Hz, 3H), 1.40(m, 2H), 1.56(m, 2H), 3.35(dt, J=6.3, 6.3Hz, 2H), 3.93(s, 3H), 5.27(s, 2H), 6.77(d, J=7.5Hz, 1H), 6.83(d, J=7.5Hz, 1H), 7.3–7.6(m, 5H), 7.58(dd, J=7.5, 8.3Hz, 1H), 8.72(brd, 1H), 9.31(brd, 1H). |
| (21)-15 | Z | 0.88(t, J=6.8Hz, 3H), 1.2–1.4(m, 6H), 1.56(m, 2H), 3.35(dt, J=6.6, 6.6Hz, 2H), 3.93(s, 3H), 5.27(s, 2H), 6.78(d, J=8.3Hz, 1H), 6.82(d, J=7.5Hz, 1H), 7.3–7.6(m, 5H), 7.57(dd, J=7.5, 8.3Hz, 1H), 8.82(brd, 1H), 9.31(brd, 1H). |
| (22)-15 | Z | 0.88(t, J=6.9Hz, 3H), 1.2–1.4(m, 6H), 1.57(m, 2H), 2.46(s, 3H), 3.36(td, J=6.5, 6.5Hz, 2H), 5.25(s, 2H), 6.81(d, J=7.5Hz, 1H), 6.84(d, J=8.6Hz, 1H), 7.3–7.6(m, 5H), 7.58(dd, J=7.5, 8.6Hz, 1H), 9.28(brd, 1H), 9.34(brd, 1H). |

TABLE 45

| Compound No. | Z/E | $^1$H-NMR (CDCl$_3$) δ |
|---|---|---|
| (3)-25 | Z | 1.64(m, 2H), 2.00(s, 3H), 3.64(q, J=6.2Hz, 2H), 3.99(s, 3H), 4.18(t, J=6.7Hz, 2H), 5.22(s, 2H), 6.94(d, J=7.0Hz, 1H), 7.3–7.55(m, 6H), 7.65(dd, J=7.0, 8.4Hz, 1H), 7.88(d, J=8.4Hz, 1H). |
| (5)-19 | Z | 2.03(s, 3H), 2.25(q, J=6.0Hz, 2H), 3.45(q, J=6.0Hz, 1H), 4.13(s, 3H), 5.25(s, 2H), 7.04(d, J=7.3Hz, 1H), 7.31–7.51(m, 5H), 7.76(dd, J=7.5Hz, 8.0Hz, 1H), 8.16(d, J=8.0Hz, 1H). |
| (11)-24 | Z | 2.01(s, 3H), 2.22(q, J=6.0Hz, 2H), 2.51(s, 3H), 3.47(q, J=6.0Hz, 2H), 5.27(s, 2H), 6.92(d, J=7.3Hz, 1H), 7.35–7.52(m, 5H), 7.75(dd, J=7.6, 8.2Hz, 1H), 7.76(brd, 1H), 8.19(J=8.1Hz, 1H). |
| (13)-24 | Z | 1.62(m, 2H), 2.02(s, 3H), 2.51(s, 3H), 3.62(q, J=6.1Hz, 2H), 4.17(t, J=6.7Hz, 2H), 5.23(s, 3H), 6.91(d, J=6.8Hz, 1H), 7.37–7.59(m, 5H), 7.63(dd, J=6.8, 8.4Hz, 1H), 7.86(d, J=8.4Hz, 1H). |

Formulation Examples using the compound of the present invention will now be described. The compounds used in the Formulation Examples and control tests are mixtures of (Z) and (E) isomers unless otherwise specified.

Formulation Example 1

Wettable Powders 20 parts by weight of each of the tetrazoyloxime derivatives shown in Tables 1 to 23 was adsorbed to 30 parts by weight of white carbon. Each tetrazoyloxime derivative adsorbed on white carbon was mixed with 3 parts by weight of sodium polyoxyethylene lauryl sulfate, 8 parts by weight of 50 wt % polyoxyethylene alkyl phenyl ether sulfate ammonium powder, 1 part by weight of sodium ligninsulfonate and 38 parts by weight of clay, and each mixture was ground using a jet mill to obtain wettable powders.

Formulation Example 2

Powders 2 parts by weight of each of the tetrazoyloxime derivatives shown in Tables 1 to 23 was mixed with 98 parts by weight of clay, and each mixture was ground to obtain powders.

Formulation Example 3

Granules 5 parts by weight of each of the tetrazoyloxime derivatives shown in Tables 1 to 23 was mixed with 90 parts by weight of a mixture of bentonite and talc in a mixing ratio of 1:1 and 5 parts of sodium alkylbenzenesulfonate, and each mixture was molded to yield granules.

The following Test Examples show that the compounds of the present invention are suited for use as active ingredients of various plant disease controlling agents. The pathopoiesis state of the test plant was examined by disease severity using a pathopoiesis index, and disease severity and control value were determined by the following equations. The results are shown in Tables 47 to 56.

Pathopoiesis Index

Samples where neither colonies nor lesions were observed are rated "0", samples where colonies and lesions were observed at about 25% are rated "1", samples where colonies and lesions were observed at about 25 to 50% are rated "2", and samples where colonies and lesions were observed at about 50% or more are rated "3", respectively.

Disease severity (%)=[Σ(number of leaves by disease severity×index)/(number of leaves examined×3 (maximum value of disease severity index))]×100

Control value (%)=(disease severity of non-treated section−disease severity of treated section)/(disease severity of non-treated section)×100

The following compounds were used as control agents.

Control agent 1: Manzeb wettable powders (commonly used downy mildew control agent)

Control agent 2: Typical compound A described in Japanese Unexamined Patent Application, First Publication No. Hei 11-269176 (WO99/29689, EP-A-1038874)

Control agents 3 and 4: Typical compounds B and C described in Japanese Unexamined Patent Application, First Publication No. 2001-55387 (WO00/75138, EP-A-1184382)

An active ingredient of manzeb wettable powders used as the control agent 1 is an agricultural fungicide which was developed by Rohm and Haas Agricultural Chemicals in USA and register on 1969, and is zinc-coordinated ethylenebisdithiocarbamate represented by the formula:

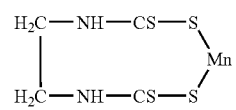

The control agents 2, 3 and 4 are compounds specified by the following general formula and the following table.

TABLE 46

$$\text{CH}_3-\underset{\underset{\text{CH}_3}{|}}{\overset{\overset{\text{CH}_3}{|}}{\text{C}}}-\text{CO}-\text{NH}-\underset{\underset{\text{N}}{\nwarrow}}{\overset{\text{S}}{\diagup}}\underset{\text{CH}_2}{\overset{\text{Q}}{|}}$$

| | R | X | Y | Z | Q |
|---|---|---|---|---|---|
| Control agent 2 | H | CH | S | CH | H |
| Control agent 3 | Cl | N | S | CH | H |
| Control agent 4 | H | CH | CH | N | Cl |

The control effect against downy mildew on grape and late blight on tomato mainly includes a protecting effect and a therapeutic effect. The protecting effect is an effect obtained by spraying a test substance on young test plants in pots, drying in air, spray-inoculating a dispersion of spores of the objective plant pathogens, standing the young test plants in pots under high humidity conditions, thereby to allow disease to develop, and growing the young test plants in pots in a greenhouse for a fixed period. The therapeutic effect is an effect obtained by inoculating a dispersion of spores of the objective plant pathogens on a young test plants in pots, standing the young test plants in pots under high humidity conditions, thereby to allow disease to develop, spraying a test substance on the young test plants in pots, drying in air, and growing the young test plants in pots in a greenhouse for a fixed period.

The test with regard to the protecting effect to the compound of the present invention was carried out against downy mildew on grape and late blight on tomato, together with control agents 1, 2, 3 and 4. All compounds of the present invention exhibited effects superior to those of the control agent 1 and also exhibited effects which were the same as or superior to those of the control agents 2, 3 and 4. The test with regard to the therapeutic effect was carried out according to the following grape downy mildew control test (Test Example 1) and tomato late blight control test (Test Example 2).

Test Example 1

Grape Downy Mildew Control Test (Therapeutic Effect)

A dispersion of spores of downy mildew (*Plasmopara viticola*) on grape was spray-inoculated on grape plants (variety: Neomuscat, 5- to 6-leaf stage) cultivated in 1/10,000 ares Wagner pots and inoculated pots were placed in a wet room maintained at 25° C. for 18 hours. After drying leaves in air, wettable powders prepared according to the method of Preparation Example 1 were diluted with water to prepare a chemical solution having an active ingredient concentration of 100 ppm. The chemical solution was sprayed enough to drip from leaf surfaces and were then transferred to a greenhouse to allow disease to develop. After 10 days had passed since inoculation, disease severity was determined. The results are shown in Tables 47 to 56.

TABLE 47

| Compound No. | Concentration (ppm) | Control value (%) |
|---|---|---|
| (1)-6 | 100 | 70 |
| (1)-7 | 100 | 100 |
| (1)-8 | 100 | 70 |
| (1)-12 | 100 | 100 |
| (1)-16 | 100 | 70 |
| (1)-18 | 100 | 100 |
| (1)-21 | 100 | 70 |
| (2)-7 | 100 | 90 |
| (2)-11 | 100 | 100 |
| (2)-12 | 100 | 90 |
| (2)-16 | 100 | 90 |
| (3)-2 | 100 | 70 |
| (3)-3 | 100 | 90 |
| (3)-4 | 100 | 90 |
| (3)-5 | 100 | 100 |
| (3)-8 | 100 | 100 |
| (3)-9 | 100 | 100 |
| (3)-15 | 100 | 100 |
| (3)-16 | 100 | 100 |
| (3)-18 | 100 | 100 |
| (3)-21 | 100 | 70 |
| (3)-22 | 100 | 100 |
| (3)-23 | 100 | 80 |

TABLE 48

| Compound No. | Concentration (ppm) | Control value (%) |
|---|---|---|
| (4)-9 | 100 | 80 |
| (4)-15 | 100 | 70 |
| (4)-18 | 100 | 70 |
| (5)-12 | 100 | 100 |
| (5)-14 | 100 | 90 |
| (6)-2 | 100 | 70 |
| (6)-6 | 100 | 70 |
| (6)-7 | 100 | 100 |
| (6)-15 | 100 | 70 |
| (7)-1 | 100 | 70 |
| (7)-3 | 100 | 80 |
| (7)-11 | 100 | 70 |
| (7)-12 | 100 | 100 |
| (8)-2 | 100 | 70 |
| (8)-7 | 100 | 70 |
| (8)-10 | 100 | 70 |
| (8)-17 | 100 | 90 |

TABLE 49

| Compound No. | Concentration (ppm) | Control value (%) |
|---|---|---|
| (9)-1 | 100 | 100 |
| (9)-2 | 100 | 70 |
| (9)-3 | 100 | 70 |
| (9)-4 | 100 | 100 |
| (9)-5 | 100 | 100 |
| (9)-6 | 100 | 70 |
| (9)-7 | 100 | 100 |
| (9)-9 | 100 | 100 |
| (9)-10 | 100 | 100 |
| (9)-11 | 100 | 100 |
| (11)-4 | 100 | 70 |
| (11)-5 | 100 | 70 |
| (11)-6 | 100 | 70 |
| (11)-7 | 100 | 100 |
| (11)-8 | 100 | 100 |
| (11)-11 | 100 | 70 |
| (11)-12 | 100 | 100 |
| (11)-21 | 100 | 70 |
| (12)-6 | 100 | 80 |
| (12)-7 | 100 | 90 |

TABLE 49-continued

| Compound No. | Concentration (ppm) | Control value (%) |
|---|---|---|
| (12)-12 | 100 | 90 |
| (12)-18 | 100 | 90 |

TABLE 50

| Compound No. | Concentration (ppm) | Control value (%) |
|---|---|---|
| (13)-5 | 100 | 70 |
| (13)-8 | 100 | 90 |
| (13)-9 | 100 | 100 |
| (13)-15 | 100 | 80 |
| (13)-21 | 100 | 80 |
| (13)-22 | 100 | 100 |
| (14)-5 | 100 | 70 |
| (16)-3 | 100 | 70 |
| (17)-1 | 100 | 100 |
| (18)-1 | 100 | 100 |

TABLE 51

| Compound No. | Concentration (ppm) | Control value (%) |
|---|---|---|
| (19)-1 | 100 | 100 |
| (19)-11 | 100 | 80 |
| (19)-12 | 100 | 90 |
| (19)-13 | 100 | 100 |
| (19)-14 | 100 | 80 |
| (19)-16 | 100 | 100 |
| (19)-23 | 100 | 70 |
| (19)-25 | 100 | 90 |
| (19)-28 | 100 | 100 |
| (19)-29 | 100 | 80 |
| (19)-31 | 100 | 90 |
| (19)-33 | 100 | 100 |
| (19)-34 | 100 | 80 |
| (19)-35 | 100 | 70 |
| (20)-1 | 100 | 70 |
| (22)-2 | 100 | 70 |
| (22)-5 | 100 | 100 |
| (22)-15 | 100 | 100 |
| Control agent 1 | 750 | 0 |
| Control agent 2 | 100 | 50 |
| Control agent 3 | 100 | 30 |
| Control agent 4 | 100 | 20 |

Test Example 2

Tomato Late Blight Control Test (Therapeutic Effect)

A dispersion of spores of late blight (*Plasmopara viticola*) on tomato was spray-inoculated on tomato plants (variety: Hofuku, 4-leaf stage) cultivated in plastic pots having a diameter of 9 cm and inoculated pots were placed in a wet room maintained at 20° C. for 18 hours. After drying leaves in air, wettable powders prepared according to the method of Preparation Example 1 were diluted with water to prepare a chemical solution having an active ingredient concentration of 100 ppm. The chemical solution was sprayed enough to drip from leaf surfaces and were then transferred to a greenhouse to allow disease to develop. After 7 days had passed since inoculation, disease severity was determined. The results are shown in Tables 52 to 56.

TABLE 52

| Compound No. | Concentration (ppm) | Control value (%) |
|---|---|---|
| (1)-6 | 100 | 90 |
| (1)-7 | 100 | 100 |
| (1)-8 | 100 | 90 |
| (1)-12 | 100 | 100 |
| (1)-16 | 100 | 100 |
| (1)-18 | 100 | 100 |
| (1)-21 | 100 | 90 |
| (2)-7 | 100 | 100 |
| (2)-11 | 100 | 100 |
| (2)-12 | 100 | 100 |
| (2)-16 | 100 | 100 |
| (3)-2 | 100 | 90 |
| (3)-3 | 100 | 100 |
| (3)-4 | 100 | 100 |
| (3)-5 | 100 | 100 |
| (3)-8 | 100 | 100 |
| (3)-9 | 100 | 100 |
| (3)-15 | 100 | 100 |
| (3)-16 | 100 | 100 |
| (3)-18 | 100 | 100 |
| (3)-21 | 100 | 100 |
| (3)-22 | 100 | 100 |
| (3)-23 | 100 | 100 |

TABLE 53

| Compound No. | Concentration (ppm) | Control value (%) |
|---|---|---|
| (4)-9 | 100 | 100 |
| (4)-15 | 100 | 80 |
| (4)-18 | 100 | 90 |
| (5)-12 | 100 | 100 |
| (5)-14 | 100 | 100 |
| (6)-2 | 100 | 80 |
| (6)-6 | 100 | 80 |
| (6)-7 | 100 | 100 |
| (6)-15 | 100 | 90 |
| (7)-1 | 100 | 80 |
| (7)-3 | 100 | 80 |
| (7)-11 | 100 | 80 |
| (7)-12 | 100 | 100 |
| (8)-2 | 100 | 90 |
| (8)-7 | 100 | 80 |
| (8)-10 | 100 | 90 |
| (8)-17 | 100 | 80 |

TABLE 54

| Compound No. | Concentration (ppm) | Control value (%) |
|---|---|---|
| (9)-1 | 100 | 100 |
| (9)-2 | 100 | 80 |
| (9)-3 | 100 | 90 |
| (9)-4 | 100 | 100 |
| (9)-5 | 100 | 100 |
| (9)-6 | 100 | 100 |
| (9)-7 | 100 | 100 |
| (9)-9 | 100 | 100 |
| (9)-10 | 100 | 100 |
| (9)-11 | 100 | 100 |
| (11)-4 | 100 | 80 |
| (11)-5 | 100 | 80 |
| (11)-6 | 100 | 80 |
| (11)-7 | 100 | 100 |
| (11)-8 | 100 | 100 |
| (11)-11 | 100 | 80 |
| (11)-12 | 100 | 100 |
| (11)-21 | 100 | 90 |
| (12)-6 | 100 | 100 |
| (12)-7 | 100 | 100 |

TABLE 54-continued

| Compound No. | Concentration (ppm) | Control value (%) |
|---|---|---|
| (12)-12 | 100 | 100 |
| (12)-18 | 100 | 100 |

TABLE 55

| Compound No. | Concentration (ppm) | Control value (%) |
|---|---|---|
| (13)-5 | 100 | 90 |
| (13)-8 | 100 | 100 |
| (13)-9 | 100 | 100 |
| (13)-15 | 100 | 90 |
| (13)-21 | 100 | 100 |
| (13)-22 | 100 | 100 |
| (14)-5 | 100 | 80 |
| (16)-3 | 100 | 80 |
| (17)-1 | 100 | 100 |
| (18)-1 | 100 | 100 |

TABLE 56

| Compound No. | Concentration (ppm) | Control value (%) |
|---|---|---|
| (19)-1 | 100 | 100 |
| (19)-11 | 100 | 90 |
| (19)-12 | 100 | 100 |
| (19)-13 | 100 | 100 |
| (19)-14 | 100 | 100 |
| (19)-16 | 100 | 100 |
| (19)-23 | 100 | 80 |
| (19)-25 | 100 | 90 |
| (19)-28 | 100 | 100 |
| (19)-29 | 100 | 100 |
| (19)-31 | 100 | 100 |
| (19)-33 | 100 | 100 |
| (19)-34 | 100 | 100 |
| (19)-35 | 100 | 80 |
| (20)-1 | 100 | 80 |
| (22)-2 | 100 | 90 |
| (22)-5 | 100 | 100 |
| (22)-15 | 100 | 100 |
| Control agent 1 | 750 | 10 |
| Control agent 2 | 100 | 60 |
| Control agent 3 | 100 | 40 |
| Control agent 4 | 100 | 30 |

As is apparent from the results shown in the tables described above, the tetrazoyloxime derivative of the present invention is superior, in therapeutic effect, to a conventional hetero ring-substituted oxime derivative and a commonly used plant disease controlling agent. Since a plant disease controlling agent containing the tetrazoyloxime derivative of the present invention, which is superior in therapeutic effect, has sufficient plant disease controlling activity even when it is sprayed after confirming pathopoiesis of plant pathogens, it is made possible to reduce the number of applications of an agricultural chemical, and thus the plant disease controlling agent is excellent in view of saving of labor and cost.

INDUSTRIAL APPLICABILITY

The tetrazoyloxime derivative represented by the general formula (1) of the present invention is less likely to cause chemical injury to useful plants and is also suited for use as an agricultural chemical, especially a plant disease controlling agent. The agricultural chemical containing the tetrazoyloxime derivative as an active ingredient of the present invention is superior in therapeutic effect against plant diseases to a conventional hetero ring-substituted oxime derivative, and is therefore suited for use as a plant disease controlling agent. Furthermore, tetrahydroxyimino derivatives represented by the general formulas (6) and (7) according to the present invention are suited for use as an intermediate of the tetrazoyloxime derivative represented by the general formula (1) of the present invention.

The invention claimed is:

1. A tetrazoyloxime compound represented by formula (1):

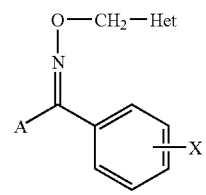

wherein X represents a hydrogen atom, a halogen atom, an alkyl group, an alkoxy group, a cyano group, a methanesulfonyl group, a nitro group, a trifluoromethyl group, or an aryl group; A represents a tetrazoyl group represented by formula (2):

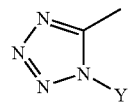

wherein Y represents an alkyl group) or a tetrazoyl group represented by formula (3):

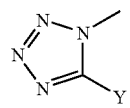

(wherein Y represents an alkyl group); and Het represents a pyridyl group represented by formula (4):

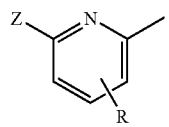

(wherein R represents a hydrogen atom or a halogen atom; Z represents a hydrogen atom, an amino group, formula QC(=O)NH— (Q represents a hydrogen atom, an alkyl group having 1 to 8 carbon atoms, an alkyl group having 1 to 6 carbon atoms substituted with a halogen atom, a cycloalkyl group having 3 to 6 carbon atoms, an alkoxyl group having 1 to 8 carbon atoms, a cycloalkyloxy group having 3 to 6 carbon atoms, a benzyloxy group, a 2-phenylethyloxy group, a thioalkyl group substituted with an alkyl group having 1 to 4 carbon atoms, an alkyl group having 1 to 2 carbon atoms substituted with an alkoxyl group having 1 to 4 carbon atoms, an alkyl group having 1 to 6 carbon atoms substituted with an acylamino group having 1 to 4 carbon atoms, an alkoxy group having 1 to 6 carbon atoms substituted with an acylamino group having 1 to 4 carbon atoms, an alkylamino group having 1 to 8 carbon atoms, an alkenyl group having 2 to 6 carbon atoms, an aralkyl group, or a phenyl group)), or a thiazoyl group represented by formula (5):

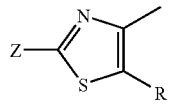

(wherein R and Z are as defined in formula (4).

2. The tetrazoyloxime compound according to claim 1, wherein Z is a group represented by formula:

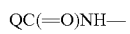

(wherein Q represents an alkyl group having 1 to 8 carbon atoms or an alkoxyl group having 1 to 8 carbon atoms) and Het is a pyridyl group represented by formula (4).

3. The tetrazoyloxime compound according to claim 2, wherein X is a hydrogen atom or a halogen atom.

4. The tetrazoyloxime compound according to claim 2, wherein Y is a methyl group.

5. The tetrazoyloxime compound according to claim 1, wherein Z is a group represented by formula:

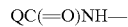

(wherein Q represents an alkyl group having 1 to 8 carbon atoms or an alkoxyl group having 1 to 8 carbon atoms) and Het is a thiazoyl group represented by the formula (5).

6. The tetrazoyloxime compound according to claim 5, wherein X is a hydrogen atom or a halogen atom.

7. The tetrazoyloxime compound according to claim 5, wherein Y is a methyl group.

8. The tetrazoyloxime compound according to claim 3, wherein Y is a methyl group.

9. The tetrazoyloxime compound according to claim 6, wherein Y is a methyl group.

10. An agricultural composition comprising the tetrazoyloxime compound of any one of claims 1 to 7 and 8 to 9 as an active ingredient and an agriculturally acceptable carrier.

11. A method for preparing a plant disease controlling composition comprising the tetrazoyloxime compound of any one of claims 1 to 7 and 8 9 as an active ingredient and an agriculturally acceptable carrier.

* * * * *